United States Patent
Wang et al.

(10) Patent No.: US 6,964,762 B2
(45) Date of Patent: Nov. 15, 2005

(54) COMPOSITION AND METHOD FOR STIMULATING IMMUNE RESPONSE TO PATHOGEN USING COMPLEX ADENOVIRAL VECTOR

(75) Inventors: Danher Wang, Mt. Pleasant, SC (US); Jianyun Dong, Mt. Pleasant, SC (US)

(73) Assignee: Genphar, Inc., Mt. Pleasant, SC (US)

( * ) Notice: Subject to any disclaimer, the term of this patent is extended or adjusted under 35 U.S.C. 154(b) by 0 days.

(21) Appl. No.: 10/327,294

(22) Filed: Dec. 19, 2002

(65) Prior Publication Data

US 2004/0028652 A1 Feb. 12, 2004

Related U.S. Application Data

(62) Division of application No. 09/585,599, filed on Jun. 2, 2000, now Pat. No. 6,544,780.

(51) Int. Cl.$^7$ .................. C12N 15/80; C12N 15/83; C12N 15/86; C12N 15/861; A61K 39/21
(52) U.S. Cl. ............... 424/93.2; 435/320.1; 424/205.1; 424/233.1; 424/199.1; 424/85.2
(58) Field of Search ............................. 424/93.1, 93.2, 424/227.1, 208.1, 228.1, 231.1, 199.1; 435/320.1

(56) References Cited

U.S. PATENT DOCUMENTS

| | | | |
|---|---|---|---|
| 5,824,544 A | 10/1998 | Armentano et al. | 435/320.1 |
| 5,866,131 A | 2/1999 | Ramshaw et al. | |
| 5,866,136 A | 2/1999 | Ramshaw et al. | |
| 6,511,845 B1 * | 1/2003 | Davis et al. | 435/320.1 |

FOREIGN PATENT DOCUMENTS

| | | |
|---|---|---|
| FR | WO 98/22606 | 5/1998 |
| WO | WO 88/00971 | 2/1988 |
| WO | WO 96/11279 | 4/1996 |
| WO | WO 98/17799 | 4/1998 |
| WO | WO 99/32147 | 7/1999 |
| WO | WO99/43839 | 9/1999 |

OTHER PUBLICATIONS

Chanda et al. J. Gene. Virol. 1990, vol. 7, pp. 67–77.*
Vernon et al. J. Gene. Virol. 1991, vol. 72, pp. 1243–1251.*
Bruce et al. J. Gene. Virol. 1990, vol. 80, pp. 2621–2628.*
Vernon et al. J. Gen. Virol. 1991, vol. 72 (pt6), pp. 1243–1251.*
Bramson et al. Human Gene Therapy 1996, vol. 7, pp. 333–342.*
Ling Xu et al., XP–002131515, *Immunization For Ebola Virus Infection*, Jan. 1998, pp. 37–42.
Ruff A. Nelle et al. XP 001053714, *Improved DNA Vaccines Against Ebola Virus*, pp. 330–331.

Jean–Luc Imler, *Adenovirus Vectors As Recombinant Viral Vaccines*, Vaccine 1995 vol. 13 No. 13, pp. 1143–1151.
Lorna Vanderzanden, et al., XP–002131516, *DNA Vaccines Expressing Either the GP or NP Genes of Ebola Virus Protect Mice From Lethal Challenge*, 1998, pp. 134–144.
Gaetano Romano et al., XP–002190944, *Latest Developments in Gene Transfer Technology: Achievements, Perspectives, and Controversies over Therapeutic Applications*, 2000, pp 19–39.
V. Randrianarison–Jewtoukoff et al., XP–002190945, Recombinant Adenoviruses as Vaccines, 1995, pp 145–157.
He et al., P.N.A.S. USA 1996, vol. 93, pp. 7274–7278.
Danthinne J. Virol. Methods 1999, vol. 81, pp. 11–20.
Gorziglia et al., J. Virol. 1999, vol. 73, pp. 6048–6055.
Bett et al., P.N.A.S. USA 1994, vol. 901, pp. 8802–8806.
Amalfitano et al., J. Virol. 1998, vol. 72, pp. 926–933.
Pasquini et al., J. Immunology and cell Biology 1997, vol. 75, pp. 397–401.
Imler, J–L: "Adenovirus Vectors As Recombinant Viral Vaccines" Vaccine, Butterworth Scientific, 1995, vol. 13, No. 13, pp. 1143–1151 Guildford, GB.
Cohen Adem D et al: "Modulating the Immune Response to Genetic Immunization" Faseb Journal, Fed. of American Soc. for Experimental Biology, Bethesda, MD; US, Dec. 1998, pp. 1611–1626, vol. 12, No. 15.
Robinson H I: "New Hope For An Aids Vaccine" Nature Reviews. Immunology,Apr. 2002, vol. 2, No. 4, pp. 239–250.

* cited by examiner

*Primary Examiner*—James Housel
*Assistant Examiner*—Bao Qun Li
(74) *Attorney, Agent, or Firm*—Benjamin Aaron Adler

(57) ABSTRACT

Genetic vaccines and methods are provided for enhancing the immunity of a host such as a human to one or more pathogens. In one aspect, a method of enhancing the immunity of a host to a pathogen is provided. The method comprises administering to the host a recombinant virus comprising an antigen sequence that is heterologous to a native progenitor of the recombinant adenovirus and encodes a viral antigen from a pathogenic virus, expression of which is under the transcriptional control of a first promoter; and a cytokine sequence that is heterologous to the native progenitor of the recombinant adenovirus and encodes a cytokine, expression of which is under the transcriptional control of a second promoter. Expression of the antigen and cytokine sequences elicits an immune response directed against the viral antigen upon infection of the host by the recombinant virus. The method can be used for immunizing a host against a wide variety of pathogen viruses, such as HIV, Ebola virus, Marburg virus, hepatitis B virus, hepatitis C virus, influenza virus, human simplex virus, human papilloma virus and respiratory syncytial virus.

20 Claims, 6 Drawing Sheets

FIGURE 2

| | | |
|---|---|---|
| DNA | RNA editing signal<br>————— TTT TTT T ————————<br>[SEQ ID NO: 1] | |
| Unedited RNA | ————— UUU UUU U ——— UAA ————<br>                                        stop codon<br>[SEQ ID NO: 2] | |
| Edited RNA | ————— UUU UUU ————————<br>                                -1 frame<br>[SEQ ID NO: 6] | |
| Modified DNA | Editing signal deleted<br>————— TTC TTC ————————<br>[SEQ ID NO: 8] | |
| mRNA | ————— UUC UUC ————————<br>                              no stop codon until the end of GP<br>[SEQ ID NO: 7] | |

SEQUENCE LISTING

<160> NUMBER OF SEQ ID NOS: 8

<210> SEQ ID NO 1
<211> LENGTH: 7
<212> TYPE: DNA
<213> ORGANISM: Ebola virus

-continued

```
<400> SEQUENCE: 1 tttttt                                                              7

<210> SEQ ID NO 2
<211> LENGTH: 7
<212> TYPE: RNA
<213> ORGANISM: Ebola virus

<400> SEQUENCE: 2 uuuuuuu                                                             7

<210> SEQ ID NO 3
<211> LENGTH: 8
<212> TYPE: RNA
<213> ORGANISM: Artificial sequence
<220> FEATURE:
<223> OTHER INFORMATION: Modified RNA editing site

<400> SEQUENCE: 3 uucuucuu                                                            8

<210> SEQ ID NO 4
<211> LENGTH: 7
<212> TYPE: DNA
<213> ORGANISM: Ebola virus

<400> SEQUENCE: 4 aaaaaaa                                                             7

<210> SEQ ID NO 5
<211> LENGTH: 8
<212> TYPE: DNA
<213> ORGANISM: Artificial sequence
<220> FEATURE:
<223> OTHER INFORMATION: DNA of modified RNA editing site

<400> SEQUENCE: 5 aagaagaa                                                            8

<210> SEQ ID NO 6
<211> LENGTH: 6
<212> TYPE: RNA
<213> ORGANISM: Ebola virus

<400> SEQUENCE: 6 uuuuuu                                                              6

<210> SEQ ID NO 7
<211> LENGTH: 6
<212> TYPE: RNA
<213> ORGANISM: Artificial sequence
<220> FEATURE:
<223> OTHER INFORMATION: Modified RNA editing site

<400> SEQUENCE: 7 uucuuc                                                              6

<210> SEQ ID NO 8
<211> LENGTH: 6
<212> TYPE: DNA
```

```
<213> ORGANISM: Artificial sequence
<220> FEATURE:
<223> OTHER INFORMATION: DNA of modified RNA editing site

<400> SEQUENCE: 8 ttcttc                                                                    6
```

COMPOSITION AND METHOD FOR STIMULATING IMMUNE RESPONSE TO PATHOGEN USING COMPLEX ADENOVIRAL VECTOR

RELATIONSHIP TO PARENT AND CO-PENDING APPLICATION

This application is a divisional application of U.S. Patent Application entitled "GENETIC VACCINE THAT MIMICS NATURAL VIRAL INFECTION AND INDUCES LONG-LASTING IMMUNITY TO PATHOGEN", application Ser. No. 09/585,599, Filed: Jun. 2, 2000, now U.S. Pat. No. 6,544,780, which is incorporated herein by reference.

BACKGROUND OF THE INVENTION

1. Field of the Invention

This invention relates to vaccines for stimulating immune responses in human and other hosts, and, in particular, relates to recombinant viruses that express heterologous antigens of pathogenic viruses, such as Ebola, HIV, hepatitis, and influenza viruses.

2. Description of the Related Art

Current techniques for developing vaccines are largely based on the concept of using denatured virus or purified viral proteins made from bacteria. These types of vaccines may be effective for only a limited number of infectious agents, and the protection rates are limited.

For viruses that contain membrane (envelope) glycoproteins (GPs), including the Ebola virus and the HIV virus, use of denatured virus or purified viral proteins often does not work satisfactorily. There may be several reasons for this. First, the GPs of these viruses are sensitive to the denaturing procedures so that the epitopes of the proteins are altered by the denaturing process. Second, the sugar moieties of the GPs are important antigenic determinants for neutralizing antibodies. In comparison, proteins made in bacteria are not properly glycosylated and can fold into somewhat different structures that can have antigenicities different from those of the natural viral proteins. Further, many vaccines that are based on attenuated or denatured virus provide a weak immune response to poorly immunogenic antigens. In addition, the vaccine preparations frequently offer only limited protection, not life-long immunity as desired.

Other vaccine approaches express antigens by plasmids directly injected into the body, the so-called naked DNA or DNA vaccine technology. These methods involve the deliberate introduction of a DNA plasmid carrying an antigen-coding gene by transfecting cells with the plasmid in vivo. The plasmid expresses the antigen that causes an immune response. The immune response stimulated by DNA vaccine can be very inefficient, presumably due to low levels of uptake of the plasmid and low levels of antigen expression in the cells. DNA vaccines are also characterized by an extremely short antigen expression period due to vector degradation. In addition, DNA vaccines are difficult and costly to produce in large amounts.

Replication-competent, live vaccinia viruses have also been modified for expression of the genes for hepatitis B (HBV), human immunodeficiency virus (HIV), influenza and malaria antigens. In some instances, though, the immune response of recombinant vaccines is often of limited nature and magnitude. Thus, for example, while peripheral immunization with vaccinia influenza recombinants provides good protection against lower respiratory tract infections, it fails to induce immunity in the upper respiratory tract. On the other hand, peripheral immunization with recombinant vaccines may prove ineffective when local rather than systemic immunity is required, as in, for example, the gastrointestinal tract.

Vaccination with recombinant vaccinia virus expressing Ebola virus GP has been attempted to confer partial protection in guinea pigs. Gilligan, K. J., et al., Vaccines, 97:87–92 (1997). Vaccination with DNA constructs expressing either GP or nucleocapsid protein (NP) protects mice from lethal challenge with Ebola virus. Vanderzanden, L., et al., Virology, 246(1):134–44 (1998). However, each of these approaches has its own set of limitations that make them less then ideal choices for Ebola virus vaccines in humans. For example, vaccinia virus rapidly kills vector-infected cells. Consequently, the vaccine antigen is expressed for only a short time. However, the major limitation for this type of approaches is that the replication of vaccina virus causes the immune system to react mainly to the vaccinia proteins, only small portion of the immune responses is targeted to the antigen of the pathogenic virus. This phenomenon has been termed "antigen dilution".

Previous attempts to remedy these deficiencies, including expression of vaccine antigens through viruses having stronger promoters, such as poxvirus, have not met with significant success.

As yet, no vaccine has been effective in conferring protection against HIV infection. Attempts to develop vaccines have thus far failed. Certain antibodies reactive with HIV, notably anti-GP160/120 are present at high levels throughout both the asymptomatic and symptomatic phases of the HIV infection, suggesting that rather than playing a protective role, such antibodies may in fact promote the attachment and penetration of the virus into the host cell. More significantly, current vaccines do not induce efficient cellular responses against the infected cells, the source of newly released virions.

SUMMARY OF THE INVENTION

Genetic viral vaccines are provided. These vaccines are designed to mimic natural infection of pathogenic viruses without causing diseases that are naturally associated with the pathogenic viruses in a host to be immunized, such as human, domestic animals and other mammals.

The vaccines are recombinant benign viruses that are replication deficient or incompetent. The benign viruses may be designed to express antigens from a wide variety of pathogens such as viruses, bacteria and parasites, and thus may be used to treat this wide variety of viruses, bacteria, and parasites that natively express these antigens. Infection of the benign virus causes host cells to express the antigens of the pathogenic virus and presents the antigen in its natural conformation and pathway as if the cell were infected by the pathogenic virus, and induces a strong and long-lasting immune response in the host.

In one embodiment, a recombinant benign virus is provided for eliciting an immune response in a host infected by the virus. The recombinant virus comprises: an antigen sequence heterologous to the benign virus that encodes a viral antigen from a pathogenic virus, expression of the viral antigen eliciting an immune response directed against the pathogenic virus and cells expressing the viral antigen in the host upon infection of the host by the recombinant virus; and an immuno-stimulator sequence heterologous to the benign virus that encodes an immuno-stimulator whose expression in the host enhances the immunogenicity of the viral antigen. The recombinant virus is replication-incompetent and does not cause disease that is associated with the pathogenic virus in the host In a variation of the this embodiment, the recombinant benign virus may be a replication-incompetent virus such as adenovirus, adeno-associated virus, SV40 virus, retrovirus, herpes simplex virus or vaccinia virus. Preferably, the benign virus does not have the pathologic regions of the native progenitor of the benign virus but retains its infectivity.

In a preferred embodiment, the benign virus is a replication-incompetent adenovirus, more preferably adenovirus type 5. The heterologous antigen sequence may be positioned in the E1, E3 or E4 region of the adenovirus. The immuno-stimulator sequence may be positioned in the E4, E3 or E1 region of the adenovirus.

In a variation of the preferred embodiment, the heterologous antigen sequence and the immuno-stimulator sequence are positioned in the E1, E3 or E4 region of the adenovirus, where the heterologous antigen sequence and the immuno-stimulator sequence are expressed from a promoter bicistronically via an internal ribosomal entry site or via a splicing donor-acceptor mechanism.

Expression of the viral antigen or the immuno-stimulator may be controlled by a promoter homologous to the native progenitor of the recombinant virus. Alternatively, expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

The pathogenic virus may be any pathogenic virus that causes pathogenic effects or disease in human or other animals. Thus, the recombinant benign virus can be used as a vaccine for protecting the host from infection of the pathogenic virus.

In a variation, the pathogenic virus may be various strains of human immunodeficiency virus (HIV), such as HIV-1 and HIV-2. The viral antigen may be an HIV glycoprotein (or surface antigen) such as HIV GP120 and GP41, or a capsid protein (or structural protein) such as HIV P24 protein.

In another variation, the pathogenic virus may be Ebola virus. The viral antigen may be an Ebola glycoprotein or surface antigen such as Ebola GP1 or GP2 protein.

In yet another variation, the pathogenic virus may be hepatitis virus such as hepatitis A, B, C, D or E virus. For example, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may be a surface antigen or core protein of hepatitis C virus such as NS3, NS4 and NS5 antigens.

In yet another variation, the pathogenic virus may be a respiratory syncytial virus (RSV). For example, the RSV viral antigen may be the glycoprotein (G-protein) or the fusion protein (F-protein) of RSV, for which the sequences are available from GenBank.

In yet another variation, the pathogenic virus may be a herpes simplex virus (HSV) such as HSV-1 and HSV-2. For example, the HSV viral antigen may be the glycoprotein D from HSV-2.

In yet another variation, the viral antigen may be a tumor antigen, such as Her 2 of breast cancer cells and CD20 on lymphoma cells, a viral oncogene such as E6 and E7 of human papilloma virus, or a cellular oncogene such as mutated ras.

It is noted that, other virus-associated proteins or antigens are readily available to those of skill in the art. Selection of the pathogenic virus and the viral antigen associated with the pathogenic virus is not a limiting factor in this invention.

The recombinant virus also expresses an immuno-stimulator to mimic cytokine-releasing response of a host cell upon viral infection and further augments the immune response to the viral antigen co-expressed from the recombinant virus. The immuno-stimulator may preferably be a cytokine. Examples of cytokine include, but are not limited to, interleukin-2, interleukin-8, interleukin-12, β-interferon, λ-interferon, γ-interferon, granulocyte colony stimulating factor (G-CSF), and granulocyte-macrophage colony stimulating factor (GM-CSF).

The viral antigen may be a full-length antigenic viral protein or a portion of the antigenic viral protein that contains the predominant antigen, neutralizing antigen, or epitope of the pathogenic virus. Alternatively, the viral antigen contains the constant region of glycoproteins of at least two strains of the pathogenic virus.

In a variation, the viral antigen may be a modified antigen that is mutated from a glycoprotein of the pathogenic virus such that the viral antigen is rendered non-functional as a viral component but retains its antigenicity. Such modification of the viral antigen includes deletions in the proteolytic cleavage site of the glycoprotein, and duplications and rearrangement of immunosuppressive peptide regions of the glycoprotein.

In another embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus.

According to this embodiment, the recombinant virus is preferably a replication-incompetent adeno-associated virus, SV40 virus, retrovirus, herpes simplex virus or vaccinia virus. The recombinant virus is capable of infecting the the host and preferably does not comprise pathologic regions native to the native progenitor of the recombinant virus.

Optionally, the recombinant virus includes an immuno-stimulator sequence heterologous to the recombinant virus that encodes an immuno-stimulator whose expression in the host enhances the immunogenicity of the viral antigen.

The present invention also provides viral vaccines that present multiple antigens to the host to further mimic natural infection of a native pathogenic virus and induce strong and long-lasting immune response to various strains or types of the pathogenic virus in the host.

In one embodiment, a recombinant virus is provided as a viral vaccine for eliciting an immune response in a host infected by the virus. The recombinant virus comprises: a plurality of antigen sequences heterologous to the recombinant virus, each encoding a viral antigen from a same pathogenic virus, different strains of a pathogenic virus, or different kinds of pathogenic viruses, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy in the host naturally associated with pathogenic virus.

According to the embodiment, the recombinant virus may be any virus, preferably replication-incompetent adenovirus, adeno-associated virus, SV40 virus, retrovirus, herpes simplex virus or vaccinia virus. The benign virus may also preferably have the pathologic regions of the native progenitor of the benign virus deleted but retain its infectivity.

Also according to the embodiment, the plurality of the antigen sequences may be multiple copies of the same antigen sequence or multiple antigen sequences that differ from each another.

In a variation of the embodiment, at least two of the plurality of the antigen sequences are expressed from a promoter bicistronically via an internal ribosomal entry site or via a splicing donor-acceptor mechanism.

Optionally, at least two of the plurality of the antigen sequences are expressed from a promoter to produce a fusion protein.

Also according to the embodiment, the viral genome further comprises at least one promoter heterologous to the native progenitor of the recombinant virus that controls the expression of at least two of the plurality of the antigen sequences. Examples of the promoter heterologous to the native progenitor of the recombinant virus include, but are not limited to, insulin promoter, CMV promoter and its early promoter, SV40 promoter, retrovirus LTR promoter/enhancer, the chicken cytoplasmic β-actin promoter, and inducible promoters such as tetracycline-inducible promoter.

Also according to the embodiment, the plurality of antigen sequences may be a combination of antigens from at least two strains of the pathogenic virus.

Optionally, the plurality of antigen sequences may be a combination of antigens from at least two different pathogenic viruses. For example, the plurality of antigen sequences may be a combination of antigens from HIV-1, HIV-2, herpes simplex virus type 1, herpes simplex virus type 2, Ebola virus, Marburg virus, and hepatitis A, B, C, D, and E viruses.

In a variation of the embodiment, the recombinant virus may further comprise one or more immuno-stimulator sequences that are heterologous to the benign virus and encodes an immuno-stimulator whose expression in the host enhances the immunogenicity of the viral antigen. For example, the immuno-stimulator may be a cytokine. Examples of the cytokine include, but are not limited to, interleukin-2, interleukin-4, interleukin-12, β-interferon, λ-interferon, γ-interferon, G-CSF, and GM-CSF.

According to the variation, the one or more immuno-stimulator sequences may be multiple copies of the same immuno-stimulator sequence or multiple immuno-stimulator sequences that differ from each other.

Optionally, at least two of the immuno-stimulator sequences may be expressed from a promoter multicistronically via an internal ribosomal entry site or via a splicing donor-acceptor mechanism. Alternatively, at least two of the immuno-stimulator sequences may be expressed from a promoter to form a fusion protein.

The present invention also provides genetic vaccines that elicit strong and long-lasting immune response to pathogenic bacteria. In one embodiment, a recombinant virus is provided as a genetic bacteria vaccine for eliciting an immune response in a host infected by the recombinant virus. The recombinant virus comprises: a plurality of antigen sequences heterologous to the recombinant virus, each encoding a bacterial antigen from a pathogenic bacteria, expression of the plurality of the bacterial antigen sequences eliciting an immune response directed against the bacterial antigen and cells expressing the bacterial antigen in the host upon infection of the host by the recombinant virus. The recombinant virus may preferably be replication-incompetent and not cause malignancy naturally associated with the pathogenic bacteria in the host.

The pathogenic bacteria may be any pathogenic bacteria that causes pathogenic effects or diseases in a host, such as *bacillus tuberculoses, bacillus anthracis*, and *spirochete Borrelia burgdorferi* that causes the Lyme disease in animals. The plurality of antigen sequences may encode lethal factors, protective antigen, edema factors of the pathogenic bacteria, or combinations thereof.

The present invention also provides vaccines against parasites that elicit strong and long-lasting immune response to pathogenic parasites. In one embodiment, a recombinant virus is provided as a parasite vaccine for eliciting an immune response in a host infected by the recombinant virus. The recombinant virus comprises: a plurality of antigen sequences heterologous to the benign virus, each encoding a parasitic antigen from a pathogenic parasite, expression of the plurality of the parasitic antigen sequences eliciting an immune response directed against the parasitic antigen and cells expressing the parasitic antigen in the host upon infection of the host by the recombinant virus. The recombinant virus may preferably be replication-incompetent and not cause a malignancy naturally associated with the pathogenic parasite in the host.

The pathogenic parasite may be any pathogenic parasites that cause pathogenic effects or diseases in a host, such as malaria and protozoa such as *Cryptosporidium, Eimeria, Histomonas, Leucocytozoon, Plasmodium, Toxoplasma, Trichomonas, Leishmania, Trypanosoma, Giardia, Babesia*, and *Theileria*. The plurality of antigen sequences may encode coat proteins, attachment proteins of the pathogenic parasites, or combinations thereof.

The present invention also provides pharmaceutical compositions that include the viral vaccines of the present invention. The pharmaceutical composition may include any of the recombinant viruses described above and a pharmaceutically acceptable carrier or diluent.

The pharmaceutical composition may also include an adjuvant for augmenting the immune response to the viral antigen expressed from the recombinant virus. Examples of the adjuvant include, but are not limited to, bacillus Calmette-Guerin, endotoxin lipopolysaccharide, keyhole limpet hemocyanin, interleukin-2, GM-CSF, and cytoxan.

The present invention also relates to kits. These kits may include any one or more vaccines according to the present invention in combination with a composition for delivering the vaccine to a host and/or a device, such as a syringe, for delivering the vaccine to a host.

The present invention also provides methods for enhancing the immunity of a host with the recombinant viruses described above.

In one embodiment, the method comprises: administering to the host a recombinant virus in an amount effective to induce an immune response. The in the recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the benign virus that encodes an immuno-stimulator whose expression in the host enhances the immunogenicity of the viral antigen. The recombinant virus may preferably be replication-incompetent and not cause malignancy naturally associated with the pathogenic virus in the host.

The recombinant virus may be administered to the host via any pharmaceutically acceptable route of administration. The recombinant virus may be administered to the host via a route of intramuscular, intratracheal, subcutaneous, intranasal, intradermal, rectal, oral and parental administration.

In another embodiment, a method is provided for enhancing the immunity of a host to a pathogenic virus with multiple antigens. The method comprises: administering to the host a recombinant virus in an amount effective to induce an immune response. The recombinant virus comprises: a plurality of antigen sequences heterologousto the benign virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy naturally associated with the pathogenic virus in the host.

Optionally, the recombinant virus may further comprise one or more immuno-stimulator sequences heterologous to the recombinant virus that encodes an immuno-stimulator whose expression in the host enhances the immunogenicity of the viral antigen.

In yet another embodiment, a method is provided for enhancing the immunity of a host to a pathogenic virus by using multiple recombinant viral vaccines (or viruses). Multiple recombinant viruses may carry different antigens in each recombinant virus. The multiple recombinant viruses may be administered simultaneously or step-wise to the host.

The method comprises: administering to a host a first and second recombinant viruses in an amount effective to induce an immune response. The first recombinant virus comprises: an antigen sequence heterologous to the first recombinant virus that encodes a viral antigen from a pathogenic virus, expression of the viral antigen eliciting an immune response directed against the viral antigen and cells expressing the viral antigen in the host upon infection of the host by the recombinant virus. The second recombinant virus comprises: an immuno-stimulator sequence heterologous to the recombinant virus that encodes an immuno-stimulator whose expression in the host enhances the immunogenicity of the viral antigen. The first and second recombinant viruses may preferably be replication-incompetent and not cause a malignancy naturally associated with the pathogenic virus in the host.

According to the embodiment, the first and second recombinant virus may be any benign virus, such as replication-incompetent adenovirus, adeno-associated virus, SV40 virus, retrovirus, herpes simplex virus and vaccinia virus. Optionally, both the first and second recombinant viruses may be replication-incompetent adenovirus. Also optionally, one of the first and second recombinant viruses may be recombinant adenovirus and the other may be recombinant vaccinia virus.

In yet another embodiment, a method is provided for enhancing the immunity of a host to a pathogen. The method comprises: administering to the host a recombinant virus and one or more immuno-stimulators. The recombinant virus may be any of the recombinant viruses described above. In particular, the recombinant virus comprises one or more antigen sequences heterologous to the recombinant virus that encode one or more antigens from the pathogen. Expression of the antigen elicits an immune response directed against the antigen and cells expressing the antigen in the host upon infection of the host by the recombinant virus. The recombinant virus is preferably replication-incompetent and does not cause a malignancy naturally associated with the pathogen in the host. The pathogen may be a pathogenic virus such as HIV, hepatitis virus and Ebola virus, a pathogenic bacteria or parasite.

According to this embodiment, the immuno-stimulator may be any molecule that enhances the immunogenicity of the antigen expressed by the cell infected by the recombinant virus. Preferably, the immuno-stimulator is a cytokine, including, but not limited to interleukin-2, interleukin-8, interleukin-12, β-interferon, λ-interferon, γ-interferon, granulocyte colony stimulating factor, granulocyte-macrophage colony stimulating factor, and combinations thereof. The cytokine may be administered into the host in a form of purified protein alone or formulated with one or more pharmaceutically acceptable excipients. Alternatively, the cytokine may be administered in a form of expression vector that expresses the coding sequence of the cytokine upon transfecting or transducing the cells of the host.

BRIEF DESCRIPTION OF THE FIGURES

FIG. 1A illustrates an example of a shuttle vector pLAd.Antigen carrying multiple antigen genes such as Antigen 1 and Antigen 2 which can be expressed from a $CMV_{ie}$ promoter bicistronically via a splicing donor-acceptor mechanism at the SD and SA sites.

FIG. 1B illustrates an example of a shuttle vector pRAd.Cytokines carrying multiple cytokine genes such as IL-2, INF, and IL-8 genes which can be expressed from a $CMV_{ie}$ promoter bicistronically via an internal ribosomal entry site IRES and a splicing donor-acceptor mechanism at the SD and SA sites.

FIG. 1C illustrates an example of constructing a genetic vaccine by ligating with an adenoviral backbon with a fragment that is derived from the shuttle vector pLAd.Antigen and contains multiple antigen genes and a fragment that is derived from the shuttle vector pRAd.Cytokines and contains multiple cytokine genes.

FIG. 2 illustrates the wild-type GP gene, which encodes the two forms of glycoproteins (sGP and GP), contains a RNA editing signal that results in un-edited and edited mRNAs. The sGP is synthesized from an un-edited mRNA and the GP is synthesized from an edited mRNA (having an insertion in one of the seven uridines). FIG. 2 also depicts the modifications made to the RNA to prevent the synthesis of sGP. The RNA editing site is modified from UUU UUU U to UUC UUC UU. This modification removes the editing signal and results in the mRNA coding only for the GP.

FIG. 3 illustrates the modification of the immunosuppressive peptide (IS) located in GP2.

FIGS. 4A illustrates a shuttle vector pLAd/EBO-GP carrying the GP gene of Ebola virus an antigen, and a shuttle vector pRAdIL2,4 carrying the IL-2 and IL-4 gene.

FIG. 4B illustrates the construction of a recombinant adenoviral vector by ligating an adenoviral backbone with a fragment that is derived from the shuttle vector pLAd/EBO-GP and contains the GP gene and a fragment that is derived from the shuttle vector pRAdIL2,4 and contains IL-2 and IL-4 genes.

DETAILED DESCRIPTION OF THE INVENTION

Figure 1A:
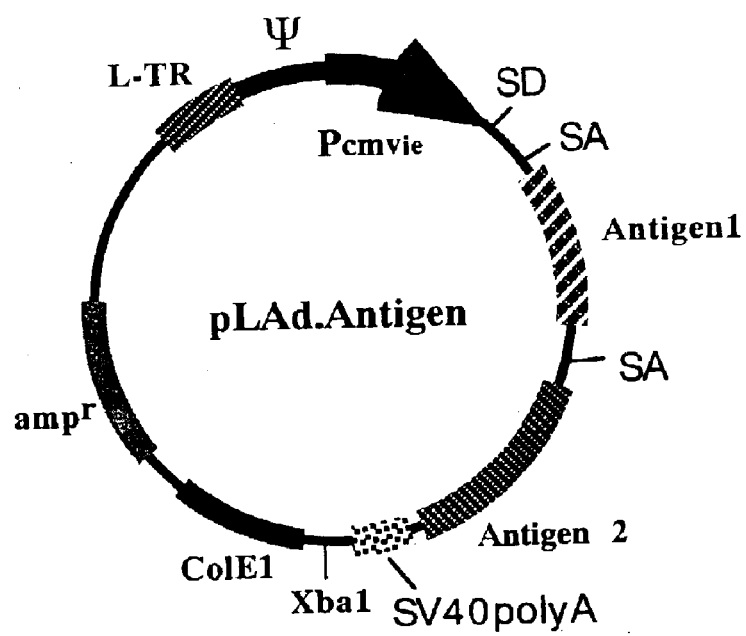
FIGS. 1A–1C illustrate an example of how to construct a genetic vaccine of the present invention.

The present invention provides genetic vaccines, pharmaceutical compositions including the vaccines and methods of immunizing a host against infection of a wide range of pathogenic viruses, bacteria and parasites. The genetic vaccines are recombinant benign viruses that are replication deficient and do not cause malignancy in the host to be immunized. Vaccination using the genetic vaccines of the present invention mimics natural viral infection in that the antigen(s) expressed by the cell infected by the genetic vaccine is presented to the host immune system in its natural conformation and by a "inside-out" mechanism, as compared with the conventional "outside-in" approach of vaccination using denatured protein or virus as a vaccine. In addition, the cell infected by the genetic vaccine also releases high levels of cytokine, thereby mimicking the natural response of the cell under stress induced by viral infection and yet not causing pathogenic effects on the cells. Mistaken by the such a "signal of pathogenic viral infection", the host immune system mounts a strong immune defense against the antigen presented by the infected cell. Therefore, in a sense, the genetic vaccine of the present invention behaves like a "sheep in wolf's clothing", presenting the viral antigen to induce a strong immune response and yet not causing the detrimental effects that the pathogens would cause on the host.

In one embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the recombinant virus that encodes an immuno-stimulator whose expression in the host enhances the immunogenicity of the viral antigen. The recombinant virus is replication-incompetent and does not cause the malignancy naturally associated with the pathogenic virus in the host.

In another embodiment, a recombinant virus is provided as a viral vaccine for eliciting an immune response against multiple antigens in a host infected by the virus. The recombinant virus comprises: a plurality of antigen sequences heterologous to the benign virus, each encoding a different viral antigen from one or more pathogenic viruses, expression of the plurality of the antigen sequences eliciting an immune response directed against the viral antigens and cells expressing the viral antigen in the host upon infection of the host by the recombinant virus. The recombinant virus may preferably be replication-incompetent and not cause the malignancy that is naturally associated with the pathogenic virus(es) in the host.

The vaccines of the present invention can be used to immunize the host against a wide variety and different strains of pathogenic viruses such as HIV-1, HIV-2, herpes simplex virus type 1, herpessimplex virus type 2, Ebola virus, Ebola virus, and hepatitis A, B, C, D, and E viruses, or pathogenic bacteria such as *bacillus tumerculoses* and *bacillus anthracis*.

The recombinant vaccine of the present invention is a recombinant virus that contains nucleic acid sequences encoding one or more viral antigens in the viral genome. When a host is immunized by the recombinant vaccine, i.e., infected by the recombinant virus, the infection of the virus in a host cell results in expression of the viral antigen which is present on the surface of the infected cell. Since expression of the viral antigen is driven by a strong promoter, expession can be maintained at a high level. Upon recognizing the large amount viral antigen on the cell surface, the host immune system mounts a strong defense against the viral antigen, thereby achieving long-lasting immunity against the pathogenic virus from which the viral antigen is derived.

Compared with immunization with vaccines that are isolated proteins expressed by bacteria, yeast or insect cells, the viral antigen expressed from the recombinant virus of the present invention better mimics the natural viral antigen in its structure and function. Isolated protein vaccine may not adopt the native conformation of the natural viral antigen and may not be properly glycosylated in the bacteria, yeast or insect cells. When such an isolated protein vaccine is injected into the host, this antigen is presented from the outside of the host cell. This conventional "outside-in" approach often does not generate strong, long-lasting immune response, presumably due to the altered antigenicity of the vaccine and quick clearance of the protein vaccine by the immune scavenging cells.

In contrast, the genetic vaccine of the present invention, i.e., the recombinant virus, presents the viral antigen by an "inside-out" mechanism. The viral antigen is expressed after infection of the recombinant virus in the host cells. This better mimics the natural production and presentation of the viral antigen by the pathogenic virus.

By using a replication incompetent virus that is incapable of spreading beyond initially infected cells, the present invention dramatically reduces the risk of side effects that may potentially be generated by using replication-competent, live virus. For example, vaccines based on live vaccinia virus can replicate in the host cells, which can impose a high level of stress on the host cell and eventually lead to cell death.

Moreover, compared to the approach of using attenuated or inactive virus as a vaccine, the process of making the genetic vaccine of the present invention is much safer. Vaccination of a large population of people or animals demand large amounts of vaccines. For virulent viruses such as Ebola virus and HIV, large-scale production of attenuated or inactive virus from the live virus can pose a great danger to the environment and people who handle the live virus.

The recombinant virus of the present invention can be used to express multiple antigen sequences simultaneously from the same viral vector. Thus, the recombinant virus may encode multiple antigens from the same strain of pathogenic virus, from different strains of the same pathogenic viruses, or from different antigens from different kind of viruses, bacteria or parasites. This enables the vaccines of the present invention to be utilized to immunize against a broad-spectrum of viruses and other infectious agents. Since these multiple antigen sequences are rearranged in the recombinant viral genome, the risk of potential recombination of these viral sequences to generate a pathogenic virus is virtually eliminated.

The genetic vaccine of the present invention also preferably express large amount of immunuo-stimulator, such as cytokine. In a natural process of viral infection, virus-infected cells display viral antigens on their surface in the context of the MHC-I receptor, while viral particles are digested by the professional antigen-presenting cells which display antigens in association with MHC-II receptors. In response to viral infection, a full range of cytokines and interferons are produced, resulting in a strong humoral and cellular response to the viral antigens. At the same, large numbers of memory cells remain to defeat any new infection. In vaccinations using isolated protein vaccines, the protein is quickly cleared by the immune scavenging cells. During this process, only MHC-II antigen presentation occurs and the cytokine-releasing response is absent or greatly diminished. As a result, little cellular response is generated and few "memory" cells are produced.

In comparison, co-expression of viral antigen and cytokine from the recombinant virus of the present invention effectively mimics the natural response of the host cell to viral infection by presenting the antigen on the surface of the infected and producing large amount of immuno-modulating cytokines. With the high levels of cytokine expressed from the host cells infected by the genetic vaccine, the host immune system would be "tricked" to mount a strong response to vaccine, thereby resulting in a longer-lasting immunity.

Additionally, although vaccination with the genetic vaccine mimics the natural viral infection of a pathogenic virus, the vaccine itself is a benign virus that does not have the detrimental effects of the pathogenic virus. For example, infection of a pathogenic virus such as HIV, influenza virus and Ebola virus has profound immuno-suppressing effects on the host, presumably due to the immuno-suppressing functions of the glycoproteins of the virus. According to the present invention, the viral antigen sequence carried by the genetic vaccine is preferred to have its pathogenic or immuno-suppressing regions deleted. In a sense, the genetic vaccine of the present invention behaves like a "sheep in wolf's clothing", presenting the viral antigen to induce strong immune response and yet not causing detrimental effects on the host.

1. The Genetic Vaccines of the Present Invention

The present invention is directed to vaccines that mimic the features of a native pathogenic virus, but without eliciting immuno-suppression and pathogenicity, thus causing the host to mount an effective defense, while not being in any actual danger of infection. The genetic vaccines are replication incompetent or defective viruses into which one or more DNA sequences encoding one or more viral antigens are inserted into the regions of the viral genome non-essential to its infectivity. The recombinant virus expresses the viral antigens and elicits a cell-mediated immune response in vivo directed against the antigens and cells expressing the antigens.

In one embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viralantigen in the host upon infection of the host by the recombinant virus; and an immuno-stimulator sequence heterologous to the recombinant virus that encodes an immuno-stimulator whose expression in the host enhances the immunogenicity of the viral antigen. The recombinant virus is replication-incompetent and does not cause a malignancy naturally associated with the pathogenic virus in the host.

The recombinant virus may be constructed from any virus as long as the native progenitor is rendered replication incompetent. For example, replication-incompetent adenovirus, adeno-associated virus, SV40 virus, retrovirus, herpes simplex virus or vaccinia virus may be used to generate the recombinant virus by inserting the viral antigen into the region non-essential to the infectivity of the recombinant virus. Therefore, it is preferred that the recombinant virus does not have the pathologic regions of the native progenitor of the benign virus but retains its infectivity to the host.

In a preferred embodiment, the recombinant virus is a replication-incompetent adenovirus.

The recombinant adenovirus of the present invention can direct high levels of antigen expression that provide strong stimulation of the immune system. The antigen expressed by cells infected by adenovirus is processed and displayed in the infected cells in a way that mimics pathogen-infected cells. This phase is believed to be very important in inducing cellular immunity against infected cells, and is completely lacking when conventional vaccination approaches are used. Further, the recombinant adenovirus may infect dendritic cells which are very potent antigen-presenting cells. Further, the recombinant adenovirus may also carry genes encoding immuno-enhancing cytokines to further boost immunity. Moreover, the recombinant adenovirus may naturally infect airway and gut epithelial cells in humans, and therefore the vaccine may be delivered through nasal spray or oral ingestion. In addition, the recombinant adenovirus of the present invention should be safe because it is replication-incompetent.

The heterologous antigen sequence may be positioned in the E1, E3 or E4 region of the adenovirus. The immuno-stimulator sequence may be positioned in the E1, E3 or E4 region of the adenovirus.

In a variation of the preferred embodiment, the heterologous antigen sequence and the immuno-stimulator sequence are positioned in the E1, E3 or E4 region of the adenovirus, where the heterologous antigen sequence and the immuno-stimulator sequence are expressed from a promoter bicistronically via an internal ribosomal entry site or via a splicing donor-acceptor mechanism.

The expression of the viral antigen or the immuno-stimulator may be controlled by a promoter homologous to the native progenitor of the recombinant virus. Alternatively, the expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

The pathogenic virus may be any pathogenic virus that causes pathogenic effects or disease in a host such as human, domestic animals or other mammals. Thus, the recombinant virus can be used as a vaccine for protecting the host from infection of the pathogenic virus.

In a variation, the pathogenic virus may be various strains of human immunodeficiency virus (HIV), such as HIV-1 and HIV-2. The viral antigen may be a HIV glycoprotein (or surface antigen) such as HIV GP120 and GP41, a capsid protein (or structural protein) such as HIV P24 protein, or other HIV regulatory proteins such as Tat, Vif and Rev proteins.

In another variation, the pathogenic virus may be influenza virus. The viral antigen may be an influenza glycoprotein such as influenza HA1, HA2 and NA.

In another variation, the pathogenic virus may be Ebola virus. The viral antigen may be an Ebola glycoprotein or surface antigen such as Ebola GP1 and GP2 protein.

In yet another variation, the pathogenic virus may be hepatitis virus such as hepatitis A, B, C, D or E virus. The viral antigen may be a surface antigen or core protein of hepatitis A, B, C, D or E virus. For example, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may also be a surface antigen or core protein of hepatitis C virus such as NS3, NS4 and NS5 antigens.

In yet another variation, the pathogenic virus may be a respiratory syncytial virus (RSV). For example, the RSV viral antigen may be the glycoprotein (G-protein) or the fusion protein (F-protein) of RSV, for which the sequences are available from GenBank.

In yet another variation, the pathogenic virus may be a herpes simplex virus (HSV) such as HSV-1 and HSV-2. For example, the HSV viral antigen may be the glycoprotein D from HSV-2.

In yet another variation, the viral antigen may be a tumor antigen or viral oncogene such as E6 and E7 of human papilloma virus, or cellular oncogenes such as mutated ras or p53.

It is noted that, other virus-associated proteins or antigens are readily available to those of skill in the art. Selection of the pathogenic virus and the viral antigen is not a limiting factor in this invention.

The viral antigen may be a full-length antigenic viral protein or a portion of the antigenic viral protein that contains the predominant antigen, neutralizing antigen, or epitope of the pathogenic virus. Alternatively, the viral antigen contains the conserved region of glycoproteins between at least two strains of the same pathogenic virus.

In a variation, the viral antigen may be a modified antigen that is mutated from a glycoprotein of the pathogenic virus such that the viral antigen is rendered non-functional as a viral component but retains its antigenicity. Such modification of the viral antigen includes deletions in the proteolytic cleavage site of the glycoprotein, and duplications and rearrangement of immunosuppressive peptide regions of the glycoprotein.

The recombinant virus also expresses an immuno-stimulator to mimic cytokine-releasing response of a host cell upon viral infection and further augments immune response to the viral antigen co-expressed from the recombinant virus. The immuno-stimulator may preferably be a cytokine. Examples of cytokine include, but are not limited to, interleukin-2, interleukin-4, interleukin-12, β-interferon, λ-interferon, =γ-interferon, granulocyte colony stimulating factor (G-CSF), and granulocyte-macrophage colony stimulating factor (GM-CSF).

In another embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus.

According to this embodiment, the recombinant virus is preferably be replication-incompetent adeno-associated virus, SV40 virus, retrovirus, herpes simplex virus or vaccinia virus. The benign virus may preferably have the pathologic regions of the native progenitor of the benign virus deleted but retains its infectivity to the host.

Optionally, the recombinant virus includes an immuno-stimulator sequence heterologous to the recombinant virus that encodes an immuno-stimulator whose expression in the host enhances the immunogenicity of the viral antigen.

The present invention also provides genetic vaccines that elicit strong and long-lasting immune response to pathogenic bacteria. In one embodiment, a recombinant virus is provided as a genetic bacteria vaccine for eliciting an immune response in a host infected by the recombinant virus. The viral genome of the recombinant virus comprises: a plurality of antigen sequences heterologous to the recombinant virus, each encoding a bacterial antigen from a pathogenic bacteria, expression of the plurality of the bacterial antigen sequences eliciting an immune response directed against the bacterial antigen and cells expressing the bacterial antigen in the host upon infection of the host by the recombinant virus. The recombinant virus may preferably be replication-incompetent and not cause a malignancy naturally associated with the pathogenic bacteria in the host.

The pathogenic bacteria may be any pathogenic bacteria that causes pathogenic effects or diseases in a host, such as *bacillus tuberculoses, bacillus anthracis*, and *spirochete Borrelia burgdorferi* that causes the Lyme disease in animals. The plurality of antigen sequences may encode lethal factors, protective antigen, edema factors of the pathogenic bacteria, or combination thereof.

The present invention also provides parasites vaccines that elicit strong and long-lasting immune response to pathogenic parasites. In one embodiment, a recombinant virus is provided as a parasite vaccine for eliciting an immune response in a host infected by the benign virus. The recombinant virus comprises: a plurality of antigen sequences heterologous to the recombinant virus, each encoding a parasitic antigen from a pathogenic parasite, expression of the plurality of the parasitic antigen sequences eliciting an immune response directed against the parasitic antigen and cells expressing the parasitic antigen in the host upon infection of the host by the recombinant virus. The recombinant virus may preferably be replication-incompetent and not a cause malignancy naturally associated with the pathogenic parasite in the host.

The pathogenic parasite may be any pathogenic parasite that causes pathogenic effects or diseases in a host, such as malaria and protozoa such as *Cryptosporidium, Eimeria, Histomonas, Leucocytozoon, Plasmodium, Toxoplasma, Trichomonas, Leishmania, Trypanosoma, Giardia, Babesia*, and *Theileria*. The plurality of antigen sequences may encode coat proteins, attachment proteins of the pathogenic parasites, or combinations thereof.

The present invention also provides viral vaccines that present multiple antigens to the host to further mimic natural infection of a native pathogenic virus and induce strong and long-lasting immune response to various strains or types of the pathogenic virus in the host.

In one embodiment, a recombinant virus is provided as a viral vaccine for eliciting an immune response in a host infected by the virus. The recombinant virus comprises: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus may preferably be replication-incompetent and not cause a malignancy naturally associated with the pathogenic virus in the host.

According to the embodiment, the recombinant virus may be any virus, preferably replication-incompetent adenovirus, adeno-associated virus, SV40 virus, retrovirus, herpes simplex virus or vaccinia virus. The recombinant virus may also preferably have the pathologic regions of the native progenitor of the benign virus deleted but retain its infectivity to the host.

Also according to the embodiment, the plurality of the antigen sequences may be multiple copies of the same antigen sequence or multiple antigen sequences that differ from each another.

In a variation of the embodiment, at least two of the plurality of the antigen sequences are expressed from a promoter bicistronically via an internal ribosomal entry site or via a splicing donor-acceptor mechanism.

Alternatively, at least two of the plurality of the antigen sequences are expressed from a promoter to form a fusion protein.

Also according to the embodiment, the recombinant virus further comprises at least one promoter heterologous to the native progenitor of the recombinant virus that controls the expression of at least two of the plurality of the antigen sequences. Examples of the promoter heterologous to the native progenitor of the recombinant virus include, but are not limited to, insulin promoter, CMV promoter andits early promoter, SV40 promoter, Rous sarcoma virus LTR promoter/enhancer, the chicken cytoplasmic β-actin promoter, and inducible promoters such as tetracycline-inducible promoter.

Also according to the embodiment, the plurality of antigen sequences may be a combination of antigens from at least two strains of the pathogenic virus.

Optionally, the plurality of antigen sequences may be a combination of antigens from at least two different pathogenic viruses. For example, the plurality of antigen sequences may be a combination of antigens from HIV-1, HIV-2, herpes simplex virus type 1, herpes simplexvirus type 2, influenza virus, Marburg virus, Ebola virus, and hepatitis A, B, C, D, and E viruses.

In a variation of the embodiment, the viral genome of the recombinant virus may further comprise one or more immuno-stimulator sequences that is heterologous to the recombinant virus and encodes an immuno-stimulator whose expression in the host enhances the immunogenicity of the viral antigen. For example, the immuno-stimulator may be a cytokine. Examples of the cytokine include, but are not limited to, interleukin-2, interleukin-4, interleukin-12, β-interferon, λ-interferon, γ-interferon, G-CSF, and GM-CSF.

According to the variation, the one or more immuno-stimulator sequences may be multiple copies of the same immuno-stimulator sequence or multiple immuno-stimulator sequences that differ from each other.

Optionally, at least two of the immuno-stimulator sequences may be expressed from a promoter bicistronically via an internal ribosomal entry site or via a splicing donor-acceptor mechanism. Alternatively, at least two of the immuno-stimulator sequences may be expressed from a promoter to form a fusion protein.

The DNA sequence encoding viral antigen(s) is inserted into any non-essential region of the replication defective virus. In the case of adenovirus, for example, the nucleic acid is preferably inserted into the E1, E3 and/or E4 region of the adenovirus and most preferably into the E4 region. Because the E1, E3 and E4 regions are available as insertion sites, the present invention also contemplates separate insertion of more than one encoding sequence.

In the recombinant viral vector vaccines of the present invention, the selected nucleotide sequences of the viral antigens are operably linked to control elements that direct transcription or expression thereof in the subject in vivo. Either homologous or heterologous viral control sequences can be employed. Useful heterologous control sequences generally include those derived from sequences encoding hostian or viral genes. Examples include, but are not limited to a cytomegalovirus (CMV) promoter such as the CMV immediate early promoter region ($CMV_{ie}$), SV40 early promoter, mouse mammary tumor virus LTR promoter, adenovirus major late promoter (AdMLP), a herpes simplex virus promoter,and a retrovirus LTR promoter. Preferably, any strong constitutive promoter may be operatively linked to viral antigens or cytokines. More preferably the viral promoter is CMV immediate early promoter ($CMV_{ie}$).

Figure 1B:
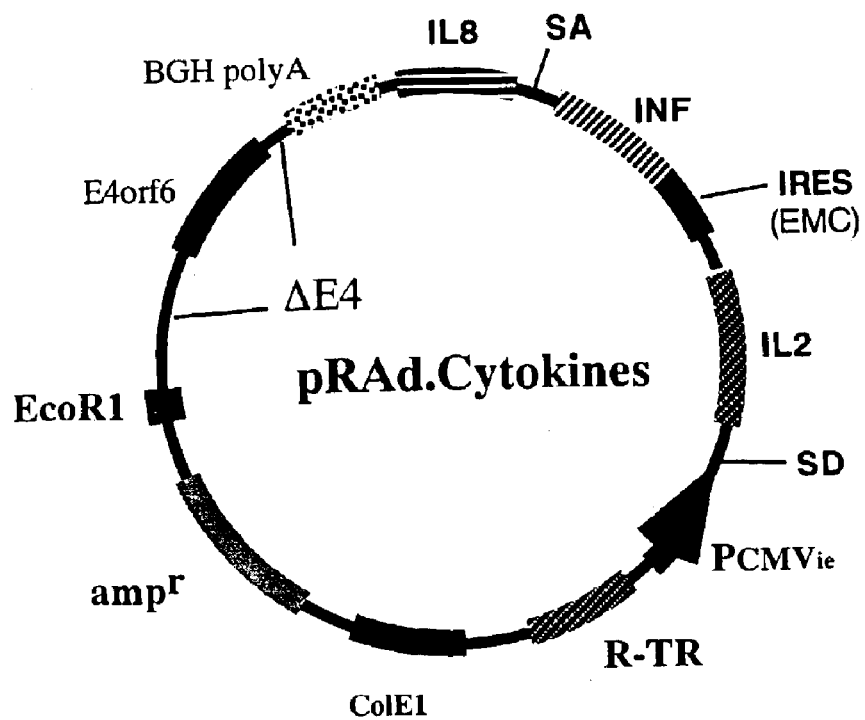
Figure 1C:
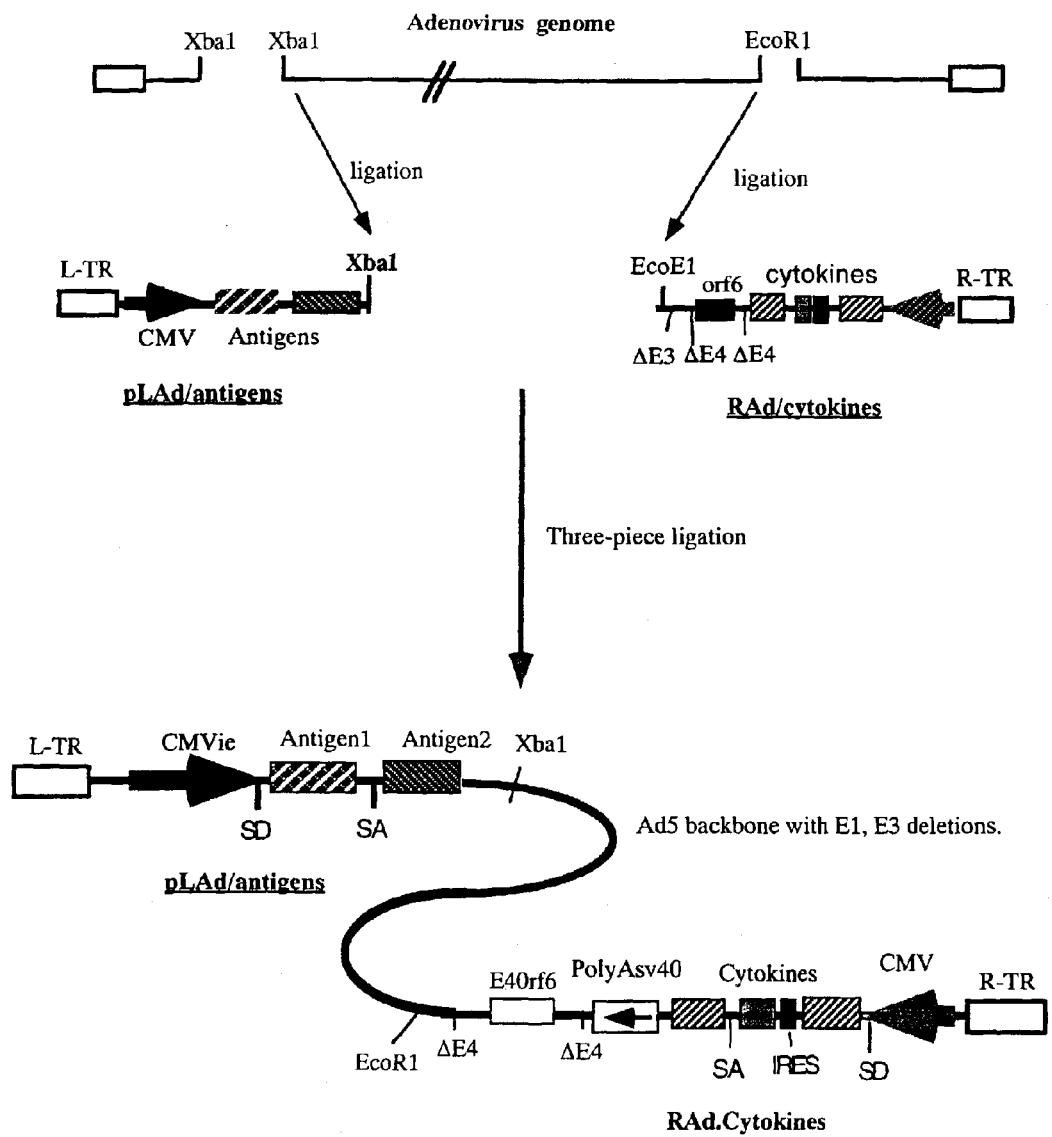

FIGS. 1A–1C illustrate a method for constructing a recombinant adenoviral vector as a genetic vaccine of the present invention. The recombinant adenoviral vector of the present invention is constructed by using shuttle plasmids or vectors carrying multiple antigen genes and multiple cytokine genes.

FIG. 1A illustrates a shuttle plasmid (pLAd.Antigen) containing two antigen genes, Antigen 1 and Antigen 2. The shuttle plasmid pLAd.Antigen contains the left end of the adenoviral genome including the left long terminal repeats L-TR, and an adenoviral packaging signal (ψ). The E1 region of the adenovirus is replaced by a multiple gene expression cassette and $CMV_{ie}$ promoter.

Genes encoding Antigen 1 and Antigen 2 are placed under the transcriptional control of the $CMV_{ie}$ promoter by a splicing mechanism at the SD and SA sites. The plasmid pLAd.Antigen also contains a SV40 polyadenylation site, as well as prokaryotic replication origin and ampicillin-resistance gene for DNA propagation in bacteria.

FIG. 1B illustrates another shuttle plasmid (pRAd.Cytokines) containing multiple cytokine genes such as IL-2, INF, and IL-8. The shuttle plasmid pRAd.Cytokines contains the right end of the adenoviral genome including the right long terminal repeats R-TR. Most of the E4 region (except orf6) is replaced by the cytokine genes. Expression of cytokine genes is under the transcriptional control of the $CMV_{ie}$ promoter via an internal ribosomal entry site (IRES) and by a splicing mechanism at the SD and SA sites. The plasmid pRAd.Cytokines also contains a bovine growth hormone (BGH) polyadenylation site, as well as a prokaryotic replication origin and ampicillin-resistance gene for DNA propagation in bacteria.

The recombinant adenoviral genome is assembled from the two shuttle plasmids, pLAd.Antigen and pRAd.Cytokines, which carries the left and right end of the adenoviral genome, respectively. The shuttle plasmids pLAd.Antigen and pRAd.Cytokines are digested with restriction enzymes such as XbaI and EcoRI, respectively.

As illustrated in FIG. 1C, the fragments corresponding to the left end and right end of adenovirus from these two shuttle plasmids, pLAd.Antigen and pRAd.Cytokines, are isolated and ligated to the middle section of the adenoviral genome (the adenovirus backbone).

The ligated vector genome DNA is then transfected into 293HK cells that express the E1 proteins of adenovirus. In the presence of E1 proteins, the vector genome in which the E1 has been deleted can replicate and be packaged into viral particle, i.e. producing the recombinant adenoviral vector that can be used as a genetic vaccine of the present invention.

Figure 5:
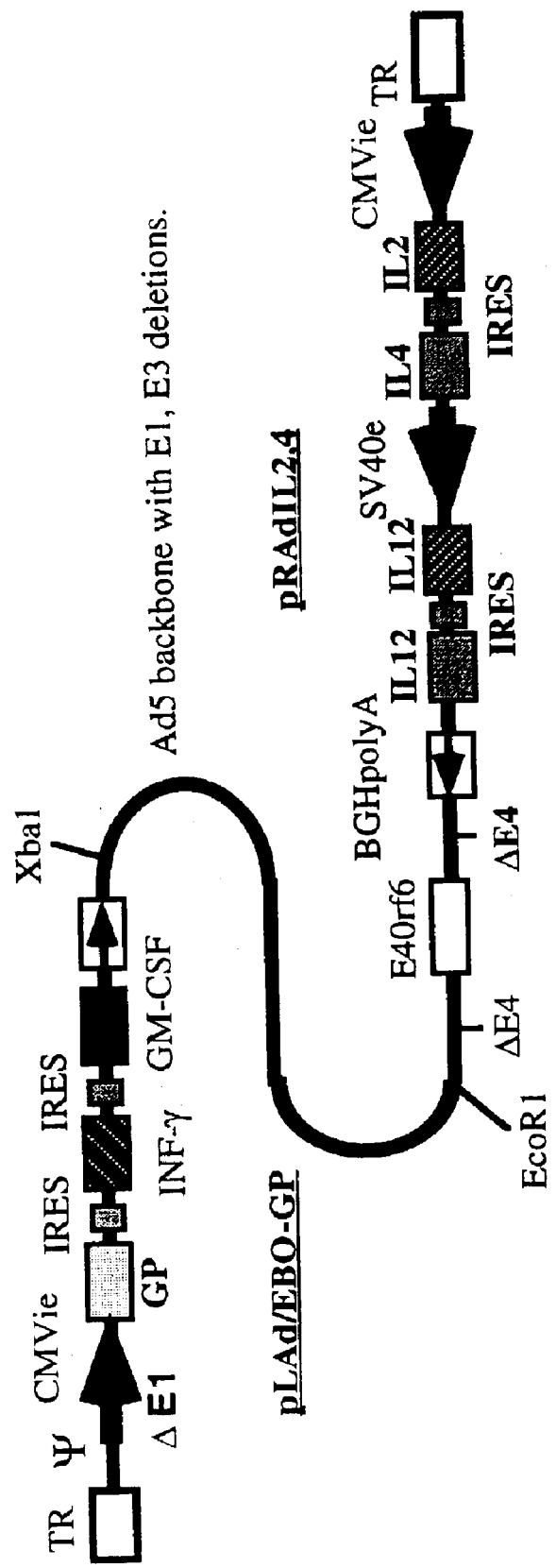
FIG. 5 illustrates a complex adenoviral vector as an example of the genetic vaccine of the present invention. The Ebola viral GP gene is expressed by a CMVie promoter in the E1 region. The GP gene is followed by INF-γ and GM-CSF which are expressed by two IRES sequences. This configuration allows for the expression of three proteins from a single mRNA. Expression of IL-2 and IL-4 is controlled by a second CMVie promoter as a bi-cistronic cassette, and followed by a second bi-cistronic cassette that expressed the two subunits of IL12 in the E4 region by a SV40 early promoter.

FIG. 5 illustrates an example of a genetic vaccine constructed by using the method described above. The replication defective adenovirus, type 5, is the vector backbone into which viral antigen and cytokines are inserted in the E1 region. The viral antigens are expressed using the CMVie promoter. The gene for the viral antigen is followed by the gene encoding INF-γ and GM-CSF, utilizing 2 IRES sequences to achieve expression of the three proteins from a single mRNA. IL2 and IL4 are controlled by a second $CMV_{ie}$ promoter as a bi-cistronic cassette, followed by a second bi-cistronic cassette that express the two subunits of IL12 in the E4 region. Those skilled in the art will appreciate that the present invention is not limited to the structure discussed above, but that alternative cytokines may be used alone or in combination with these and/or other cytokines. The detailed information about of these cytokines are described in the following section.

2. Cytokines Co-Expressed With Viral Antigens

The recombinant virus of the present invention may also express an immuno-stimulator to mimic cytokine-releasing response of a host cell upon viral infection and further augment immune response to the viral antigen co-expressed from the recombinant virus. The immuno-stimulator may be an immunoenhancing cytokine to further stimulate the immune system. The recombinant virus may encode one or multiple cytokines in any combination. Alternatively, multiple cytokines may be expressed by more than one recombinant virus or delivered to the host by using other techniques such as delivery via naked DNA plasmids or injection of cytokine proteins.

Examples of cytokine include, but are not limited to, interleukin-2, interleukin-4, interleukin-8, interleukin-12, β-interferon, λ-interferon, γ-interferon, granulocyte colony stimulating factor (G-CSF), and granulocyte-macrophage colony stimulating factor (GM-CSF).

Cytokines are immunodmodulatory molecules particularly useful in the vaccines of the invention as they are pleitropic mediators that modulate and shape the quality and intensity of the immune response. Cytokines are occasionally autocrines or endocrines, but are largely paracrine hormones produced in nature by lymphocytes and monocytes.

As used herein, the term "cytokine" refers to a member of the class of proteins or peptides that are produced by cells of the immune system and that regulate or modulate an immune response. Such regulation can occur within the humoral or the cell mediated immune response and includes modulation of the effector function of T cells, B cells, NK cells, macrophages, antigen presenting cells or other immune system cells.

Cytokines are typically small proteins or glycoproteins having a molecular mass of less than about 30 kDa. As used herein the term cytokine encompasses those cytokines secreted by lyphocytes andother cell types (often designated as lymphokines) as well as cytokines secreted by monocytes and macrophages and other cell types (often designated as monokines). As used herein, the term cytokine encompasses those cytokines secreted by lymphocytes and other cell types as well as cyotkines secreted by monocytes and macrophages and other cell types. The term cytokine includes the interleukins, such as IL-2, IL-4, IL-8 and IL-12, which are molecules secreted by leukocytes that primarily affect the growth and differentiation of hematopoietic and immune system cells. The term cytokine also includes hematopoietic growth factors and, in particular, colony stimulating factors such as colony stimulating factor-1, granulocyte colony stimulating factor and granulocyte macrophage colony stimulating factor.

The cytokines can have the sequence of a naturally occurring cytokine or can have an amino acid sequence with substantial amino acid sequence similarity, e.g., 60–95% amino acid sequence similarity, preferably 70–98% amino acid sequence, and most preferably 75–95% amino acid sequence similarity to the sequence of a naturally occurring cytokine.

Thus, it is understood that limited modifications to a naturally occurring sequence can be made without destroying the biological function of the cytokine. For example, minor modifications of gamma interferon that do not destroy its function fall within the definition of gamma interferon. These modifications can be deliberate, as through site-directed mutagenesis, or can be accidental such as through mutation. The preferred cytokines are IL-2, IL-8, IL-12, or γ-interferon, β-interferon, λ-interferon, GM-CSF, or G-CSF or a combination thereof.

Interleukin-2 is a lymphokine produced by helper T cells and is active in controlling the magnitude and type of the immune response. Smith, K. A., Ann. Rev. Immunol. 2, 319–333 (1984). Other functions have also been ascribed to IL-2 including the activation of NK cells (Minato, N. et al., J. Exp. Med. 154, 750 (1983)) and the stimulation of cell division in large granular lymphocytes and B cells. Tsudo, M. et al. J. Exp. Med. 160, 612–616 (1984). Studies in mice and humans have demonstrated that deficient immune responsiveness both in vivo and in vitro can be augmented by IL-2. For example, exogenous IL-2 can restore the immune response in cyclophosphamide-induced immuno-suppressed mice (Merluzzi, V. J. et al. Cancer Res. 41, 850–853 (1981)) and athymic (nude) mice. Wagner, H. et al. Nature 284, 278–80 (1982). Furthermore, IL-2 canrestore responsiveness of lymphocytes from patients with various immunodeficiency states such as leprosy and cancer. Vose, B. M. et al. Cancer Immuno. 13, 105–111 (1984). The genes for murine (Yokota, T. et al. Proc. Natl. Acad. Sci. USA 82, 68–72 (1985)) and human (Taniguchi, T. et al. Nature, 302, 305–307 (1983)) IL-2 have been cloned and sequenced.

Interleukin-4 is a T cell derived factor that acts as an induction factor on resting B cells, as a B cell differentiation factor and as a B cell growth factors. Sevenusar, E. Eur. J. Immunol. 17, 67–72 (1987). The gene for human IL-4 has been isolated and sequenced. Lee, F. et al. Proc. Natl. Acad. Sci. USA 83, 2061–2065 (1986).

IL-12 is a recently characterized heterodimeric cytokine that has a molecular weight of 75 kDa and is composed of disulfide-bonded 40 kDa and 35 kDa subunits. It is produced by antigen presenting cells such as macrophages, and binds to receptors on activated T, B and NK cells (Desai, B. B., et al., J. Immunol., 148:3125–3132 (1992); Vogel, L. A., et al., Int. Immunol., 8:1955–1962, (1996)). It has several effects including 1) enhanced proliferation of T cells and NK cells, 2) increased cytolytic activities of T cells, NK cells, and macrophages, 3) induction of IFN-γ production and to a lesser extent, TNF-α and GM-CSF, and 4) activation of TH1 cells. (Trinchieri, G., et al., *Blood*, 84:4008–4027 (1994). IL-12 has been shown to be an important costimulator of proliferation in Th1 clones (Kennedy et al., *Eur. J. Immunol.* 24:2271–2278 (1994)) and leads to increased production of IgG2a antibodies in serum (Morris, S. C., et al., *J. Immunol.* 152:1047–1056 (1994); Germann, T. M., et al., *Eur. J. Immunol.*, 25:823–829 (1995); Sher, A., et al., *Ann. N.Y. Acad. Sci.*, 795:202–207 (1996); Buchanan, J. M., et al., *Int. Immunol.*, 7:1519–1528 (1995); Metzger, D. W. et al., *Eur. J. Imunol.*, 27:1958–1965 (1997)). Administration of IL-12 can also temporarily decrease production of IgG1 antibodies (Morris, S. C., et al., *J. Immunol.* 152:1047–1056 (1994); McKnight, A. J., *J. Immunol.* 152:2172–2179 (1994); Buchanan, J. M., et al., *Int. Immunol.*, 7:1519–1528 (1995)), indicating suppression of the Th2 response. The purification and cloning of IL-12 are disclosed in WO 92/05256 and WO 90/05147, and in EP 322,827 (identified as "CLMF"). All of the above effects were observed in adult animals.

Interferons (IFNs) are relatively small, species-specific, single chain polypeptides, produced by hostian cells in response to exposure to a variety of inducers such as viruses, polypeptides, mitogens and the like. They exhibit antiviral, antiproliferative and immunoregulatory properties and are, therefore, of great interest as therapeutic agents in the control of cancer and various other antiviral diseases (J. Desmyter et al., *Lancet* 11, 645–647 (1976); R. Derynck et al., *Nature* 287, 193 (1980)). Human interferons are grouped into three classes based on their cellular origin and antigenicity: α-interferon (leukocytes), β-interferon (fibroblasts) and γ-interferon (B cells). Recombinant forms of each group have been developed and are commercially available.

γ-interferon is also a T cell derived molecule which has profound effects on the immune response. The molecule promotes the production of immunoglobulin by activated B cells stimulated with interleukin-2. γ-interferon also increases the expression of histocompatability antigens on cells which associated with viral antigens to stimulate cytotoxic T cells. The gene for human γ-interferon has been isolated and sequenced. Gray, P. W. et al., *Nature* 295, 503–508 (1982).

Human alpha interferons (also known as Leukocyte interferons) comprise a family of about 30 protein species, encoded by at least 14 different genes and about 16 alleles. Some of these alpha interferon protein species have been shown to have antiviral, antigrowth and immunoregulatory activities. See, e.g., Pestka et al., *Ann. Rev. Biochem.*, 56:727 (1987). The therapeutic efficacy of human alpha interferons has been established for human cancers and viral diseases. For example, recombinant interferons (IFN alpha-2a, IFN alpha-2b, IFN alpha-2c), cell-line derived interferon (IFN alpha-n1) and interferon derived from leukocytes (IFN alpha-n3) are currently used for the treatment of Condyloma acuminata, hepatitis (Weck et al., *Am. J. Med.*, 85(Suppl 2A):159 (1988); Korenman et al., *Annal. Intern. Med.*, 114.:629(1991); Friedman-Kien et al., *JAMA*, 259:533 (1988)), for the regression of some malignancies (Baron et al., *JAMA*, 266:1375 (1991)), for the treatment of AIDS related Kaposi's sarcoma (Physicians Desk Reference, 47th edit., eds. Medical Economics Data, Montvale, N.J., p. 2194 and 2006 (1993)) and are currently being considered for the treatment of human acquired immunodeficiency syndrome (AIDS) either alone or in combination with other antiviral agents (Hirsch, *Am. J. Med.*, 85(Suppl 2A):182 (1988)).

β-interferon has been shown to be a glycoprotein by chemical measurement of its carbohydrate content. It has one N-glycosidyl attachment site (E. Knight, Jr., *Proc. Nat. Acad. Sci.*, 73, 520 (1976); E. Knight, Jr., and D. Fahey, *J. Interferon Res.*, 2 (3), 421 (1982)). Even though not much is known about the kinds of sugars which make up the carbohydrate moiety of β-interferon, it has been shown that the carbohydrate moiety is not essential for its antigenicity, biological activity or hydrophobicity (T. Taniguchi et al., supra; E. Knight, Jr., supra; and E. Knight, Jr. and D. Fahey, supra). Beta-interferon can be induced in fibroblasts by viral challenge and contains about 165 amino acids. The sequence of □-interferon is known. Fiers et al. *Philos. Tmas. R. Soc. Lond., B, Biol. Sci.* 299:29–38 (1982).

GM-CSF is a cytokine important in the maturation and function of dendritic cells. It binds receptors on dendritic cells and stimulates these cells to mature, present antigen, and prime naive T cells. Dendritic cells form a system of highly efficient antigen-presenting cells. After capturing antigen in the periphery, dendritic cells migrate to lymphoid organs and present antigens to T cells. These potent antigen-presenting cells are unique in their ability to interact with active naive T cells. The potent antigen-presenting capacity of dendritic cells may be due in part to their unique life cycle and high level expression of major histocompatibility complex class I and II molecules and co-stimulatory molecules. The sequence of human GM-CSF is known. Wong et al., *Science* 228:810–815 (1985).

Granulocyte colony stimulating factor (G-CSF) is one of the hematopoietic growth factors, also called colony stimulating factors, that stimulate committed progenitor cells to proliferate and to form colonies of differentiating blood cells. G-CSF preferentially stimulates the growth and development of neutrophils, and is useful for treating in neutropenic states. Welte et al., *PNAS-USA* 82: 1526–1530 (1985); Souza et at., *Science* 232: 61–65 (1986) and Gabrilove, *J. Seminars in Hematology* 26: (2) 1–14 (1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection. See, e.g., Wendel et al., *J. Immunol.*, 149:918–924 (1992). The cDNAs for human (Nagata et al., *Nature* 319;415, 1986) and mouse G-CSF (Tsuchiya et al., *PNAS* 83, 7633, 1986) have been isolated, permitting further structural and biological characterization of G-CSF.

In humans, endogenous G-CSF is detectable in blood plasma. Jones et al., *Bailliere's Clinical Hematology* 2 (1): 83–111 (1989). G-CSF is produced by fibroblasts, macrophages, T cells trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids. Nagata et at., *EMBO J* 5: 575–581 (1986). The form comprised of 174 amino acids has been found to have the greatest specific in vivo biological activity. G-CSF is species cross-reactive, such that when human G-CSF is administered to another host such as a mouse, Canine or monkey, sustained neutrophil leukocytosis is elicited. Moore et at. *PNAS-USA* 84: 7134–7138 (1987).

The present invention provides an effective means for enhancing the immune response to the specific foreign antigenic polypeptides of recombinant viruses. Although any foreign antigenic polypeptide can be used in the vaccine of the present invention, the vaccine is particularly useful in vaccines against the HIV virus and the Ebola virus, since

3. Genetic Vaccines Against HIV Infection

The genetic vaccine of the present invention also addresses the need for an efficient vaccine against the HIV virus. According to the present invention the genetic vaccine may be a recombinant benign virus in which the viral genome carries one or more antigens from HIV, such as HIV glycoproteins (e.g. GP120 and GP41) or capsid proteins (e.g. P24). Sequences of these HIV antigens may be modified such as deletion of the immunosuppressive regions of the HIV glycoproteins.

The HIV virus causes the disease known as Acquired Immune Deficiency Syndrome (AIDS). AIDS has been described as a modern plague since its first description in 1981, it has claimed over 60,000 victims, and accounted for over 32,000 deaths in the United States alone. The disease is characterized by a long aysmptomatic period followed by a progressive degeneration of the immune system and the central nervous system. The virus may remain latent in infected individuals for five or more years before symptoms appear, and thus, the true impact of the disease has yet to be felt. Many Americans may unknowingly be infected and capable of infecting others who might come into contact with their body fluids. Thus, if unchecked, the personal, social and economic impact of AIDS will be enormous.

The HIV virus is a retrovirus. Thus, its genetic matierial is RNA, which encodes the information for viral replication. Upon infection of a host cell, the RNA acts as a template for the transcription to DNA, which is catalyzed by an enzyme called reverse transcriptase. The DNA so produced enters the cell nucleus where it is integrated into the host DNAas a provirus. When properly activated, the retroviral-derived DNA is transcribed and translated to produce RNA containing virions, which are then released from the cell by a budding process.

When an individual becomes infected with HIV, the virus preferentially attaches to and enters a particular class of white blood cells, called T4 lymphocytes, which are characterized by the presence of a cell surface marker termed CD4. These white blood cells play an integral role in the immune system, functioning as critical components of both the humoral and cellular immune response. Much of the deleterious effect of HIV can be attributed to the functional depression or destruction of T4 lymphocytes.

The intact HIV virion is roughly spherical and is approximatelyl 110 nm in diameter. The virion has an outer membrane covered with spike-like structures made up of glycoprotein, gp160/120. In addition, there exists a transmembrane protein termed gp41. Inside the virion are two structural proteins: an outer shell composed of the phosphoprotein, p17, and an inner nucleoid or central core made up of the phosphoprotein, p24. The viral RNA is present inside the core along with two copies of the reverse transcriptase enzyme, p66/51, which is necessary for the synthesis of viral DNA from the RNA template. The HIV RNA genome encodes three major structural genes: gag, pol and env, which are flanked at either end by long terminal repeat (LTR) sequences. The gag gene codes for the group-specific core proteins, p55, p39, p24, p17 and p15. The pol genes code for the reverse transcriptase, p66/p51, and the protease, p31. The env genes encode the outer envelope glycoprotein, gp120, and its precursor, gp160, and the transmembrane glycoprotein, gp41. Some of the genes tend to be highly variable, particularly the env genes. In addition, there are five other genes, not shared by other retroviruses, which are either involved in transcriptional or translational regulation or encode other structural proteins. The entire HIV genomehas now been sequenced. See Ratner et al. Nature 313:277 (1985), which is incorporated herein by reference.

The HIV envelope protein has been extensively described, and the amino acid and RNA sequences encoding HIV envelope from a number of HIV strains are known. See Myers, G. et al., *Human Retroviruses and AIDS: A compilation and analysis of nucleic acid and amino acid sequences*, Los Alamos National Laboratory, Los Alamos, N.Mex. (1992). The HIV envelope protein is a glycoprotein of about 160 kd (gp160), which is anchored in the membrane bilayer at its carboxyl terminal region. The N-terminal segment, gp120, protrudes into the aqueous environment surrounding the virion and the C-terminal segment, gp41, spans the membrane. Via a host-cell mediated process, gp160 is cleaved to form gp120 and the integral membrane protein gp41. As there is no covalent attachment between gp120 and gp41, free gp120 is released from the surface of virions and infected cells.

The gp120 molecule consists of a polypeptide coreof 60,000 daltons, which is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence, and the positions of 13 of the approximately 24 N-linked glycosylation sites in the gp120 sequence are common to all gp120 sequences. The hypervariable domainscontain extensive amino acid substitutions, insertions and deletions. Sequence variations in these domains result in up to 30% overall sequence variability between gp120 molecules from the various viral isolates. Despite this variation, all gp120 sequences preserve the virus's ability to bind to the viral receptor CD4 and to interact with gp41 to induce fusion of the viral and host cell membranes.

The HIV virus attaches to host cells by an interaction of the envelope glycoproteins with a cell surface receptor. It appears that when HIV makes contact with a T4 cell, gp120 interacts with the CD4 receptor. The viral envelope is then fused with the cell membrane and the inner core of the virus enters the infected cell where the transcription of RNA into a DNAprovirus is catalyzed by reverse transcriptase. The provirus may remain in the cell in a latent form for some months or years, during which time the infected individual is asymptomatic. However, if the virus is later activated causing viral replicationand immunosuppression the individual will than be susceptible to the opportunistic infections associated with AIDS.

By using the genetic vaccine of the present invention, non-HIV-infected individuals may be immunized against HIV. The HIV antigen expressed by the genetic vaccine may be any antigen derived from a HIV virus, such as HIV GP120, GP41, P24, Tat, Vif, and Rev protein. For HIV-infected individuals the vaccine may also be used boost their immune response and help fight against this virulent virus. Since the genetic vaccine can express high level of antigens and/or a variety of HIV glycoproteins and capsid proteins simultaneously, the vaccinated individuals should be immunized against various strains of HIV, such as HIV-1 and HIV-2. Additionally, since the genetic vaccine can express high levels of cytokines to mimic the body's response to natural viral infection, the body's immune response to such a genetic vaccine against HIV should be strong and longlasting, thereby achieving a life-long immunity against this deadly virus.

4. Genetic Vaccines Against Hepatitis Viruses

The genetic vaccine of the present invention also addresses the need for an efficient vaccine against hepatitis viruses such as hepatitis A, B, C, D, and E viruses. According to the present invention the genetic vaccine may be a recombinant benign virus in which the viral genome carries one or more antigens from a hepatitis virus, such as glycoproteins and core proteins of the hepatitis virus. Sequences of these HIV antigens may be modified such as deletion of the pathogenic regions of the hepatitis glycoproteins or coreproteins.

In particular, the recombinant virus of the present invention can be used as a vaccine to immunize individuals against Hepatitis B infections. Viral hepatitis B is caused by the Hepatitis B virus (HBV). HBV is estimated to have infected 400 million people throughout the world, making HBV one of the most common humanpathogens. Hepatocellular carcinomas (HCC), one of the most common cancers afflicting humans, is primarily caused by chronic HBV infection.

HBV is a mostly double-stranded DNA virus in the Hepadnaviridae family. The HBV genome is unique in the world of viruses due to its compact form, use of overlapping reading frames, and dependence on a reverse-transcriptase step, though the virion contains primarily DNA. The HBV genome has four genes: pol, env, pre-core and X that respectively encode the viral DNA polymerase, envelope protein, pre-core protein (which is processed to viral capsid) and protein X. The function of protein X is not clear but it may be involved in the activation of host cell genes and the development of cancer.

The diagnosis of HBV infection is generally made on the basis of serology. Virtually all individuals infected with HBV will have detectable serum hepatitis surface antigens (HBsAg). Despite notable successes of vaccines against HBV infection, it is still an on-going task. A review on modern hepatitis vaccines, including a number of key references, may be found in the Eddleston, *The Lancet*, p. 1142, May 12, 1990. See also *Viral Hepatitis and Liver Disease*, Vyas, B. N., Dienstag, J. L., and Hoofnagle, J. H., eds., Grune and Stratton, Inc. (1984) and *Viral Hepatitis and Liver Disease*, Proceedings of the 1990 International Symposium, eds F. B. Hollinger, S. M. Lemon and H. Margolis, published by Williams and Wilkins.

By using the genetic vaccine of the present invention, non-hepatitis-infected individuals may be immunized against hepatitis virus. For hepatitis virus-infected individuals the vaccine may also be used boost their immune response and help fight against the hepatitis virus. Since the genetic vaccine can express high level of antigens and/or a variety of hepatitis glycoproteins and coreproteins simultaneously, the vaccinated individuals should be immunized against various strains and/or types of hepatitis virus, such as hepatitis A, B, C, D, and E virus. For example, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may be a surface antigen or core protein of hepatitis C virus such as NS3, NS4 and NS5 antigens. Additionally, since the genetic vaccine can express high levels of cytokines to mimic the body's response to natural viral infection, the body's immune response to such a genetic vaccine against hepatitis should be strong and long-lasting, thereby achieving a life-long immunity against the hepatitis virus.

5. Genetic Vaccines Against Ebola Virus

The genetic vaccine of the present invention also addresses the need for an efficient vaccine against the deadly virus, Ebola virus. According to the present invention the genetic vaccine may be a recombinant benign virus in which the viral genome carries one or more antigens from Ebola hepatitis, such as glycoproteins (e.g. GP1 and GP2) of Ebola virus. Sequences of these Ebola antigens may be modified such as deletion of the immunosuppressive regions and/or other pathogenic regions of the Ebola virus.

Ebola virus is one of the most lethal viruses known to mankind with a mortality rate of up to 90%. Johnson, K. M., *Ann Intern Med* 91(1):117–9 (1979). Victims of Ebola virus infection are subjected to a horrible hemorrhagic diseases which kills in a matter of days. The natural reservoir of the virus remains unknown, as do the specifics of pathogenesis of the infection. The virus has a very specific tropism for liver cells and cells of the reticuloendothelial system, such as macrophages. Massive destruction of the liver is hallmark feature of the disease.

Although Ebola virus infection is rare, there is concern by public health officials about the potential for the disease to become an international epidemic as the Ebola virus is easily transmitted through human contact and is extremely contagious. Outbreaks like those that have recently occurred in Africa could happen in industrialized countries due to the rapid and extensive nature of modern travel. Recent cases of Ebola virus infection in Africa send strong warnings to be prepared for the outbreaks of this extremely dangerous infectious disease. In addition, Ebola virus has a terrifying potential if used as a biological weapon byterrorist nations or organizations. As in most cases of viral infection, the best approach to prevent an outbreak of Ebola virus is through vaccination. However, there currently is no effective vaccine nor treatment available against Ebola virus infection.

Ebola viruses are enveloped, negative strand RNA viruses, which belong to the family Filoviridae. There are three strains of filoviruses: Ebola, Marburg and Reston. The Ebola virus can enter the body a number of different ways such as an opening through which air is taken in because the virus can travel on airborne particles and it can also enter the body through any opening in the skin, such as cuts.

The Ebola virus has a non-segmented RNA genome that encodes all the viral structural proteins (nucleoprotein, matrix proteins VP24 and VP40), non-structural proteins (VP30, VP35) and viral polymerase. Peters, C. J., *West J Med* 164(1):36–8 (1996). Among the viral proteins, the envelope glycoproteins (GP) exist in two forms, a secreted glycoprotein (50–70 kDa) and a transmembrane glycoprotein (130–170 kDa) generated by transcriptional editing. Sanchez, A. et al., *Proc Natl Acad Sci U.S.A.*, 93(8):3602–7 (1996). Although the two forms of GP share 295 amino acid homology, they have distinct binding specificities, suggesting that they play different roles in the course of viral infection. The secreted glycoprotein (sGP) is the predominant form synthesized and secreted by the infected cells. It may play a role in suppressing the host immune system (Yang,Z., et al., *Science* 279(5353):1034–7 (1998)) and may serve as a decoy to allow the virus particle to escape from neutralizing antibodies, since the two forms of GPs partly share their antigenicity. Analysis of monoclonal antibodies from the human survivors of Ebola virus Zaire infection has revealed that the vast majority of them were specific to the sGP, and only a few bound weakly to GP. Maruyama, T., et al., *J Infect Dis*, 179 Suppl 1:S235–9 (1999), Maruyama, T., et al., *J Virol*, 73(7):6024–30 (1999). Although the exact mechanism by which the sGP may suppress the immune system is not clearly understood, the large amounts of sGP synthesized in the early phase of the infection are probably responsible for the inhibition of neutrophil infiltration of the infected sites (Yang, Z., et al., *Science* 279(5353):1034–7 (1998)) and the absence of humoral immune response in Ebola virus infected patients. Baize, S., et al., *Nat Med*, 5(4):423–6 (1999). This protein may also act to over-activate many types of immune cells which can lead to massive intravascular apoptosis—essentially a shut-down of the immune system. Baize, S., et al., *Nat Med*, 5(4):423–6 (1999). The importance of the sGP to the Ebola virus life-cycle is also suggested by the fact it is present in all Ebola virus strains examined to date. Feldmann, H., et al., *Arch Virol Suppl*, 15:159–69 (1999).

The membrane glycoproteins are responsible for the attachment and penetration of the virions into target cells by mediating receptor binding and viral-cellular membrane fusion. Wool-Lewis, et al., *J. Virol*, 72(4):3155–60 (1998), Ito H., et al., *J. Virol*, 73(10):8907–12 (1999). They are synthesized as a single peptide precursor and cleaved by cellular enzymes (furin or cathepsin B) into the two mature forms, GP1 and GP2. The two GPs remain associated through a disulfide bond linkage and remain anchored in the viral membrane by a transmembrane (TM) domain. Ito H., et al., *J. Virol*, 73(10):8907–12 (1999); Malashkevich, V. N., et al., *Proc Natl Acad Sci U.S.A.*, 96(6):2662–7 (1999). The proteolytic cleavage site is composed of 4–5 basic amino acid residues that are similar to those found in the GPs of retrovirus, influenza, and paramyxoviruses. Garten, W., et al., *Biochimie*, 76(3–4):217–25 (1994). The cleavage event is essential for viral infectivity and is likely carried out by the same enzymes that cleave GPs of retrovirus or influenza viruses. Garten, W., et al., *Biochimie*, 76(3–4):217–25 (1994); Volchkov, V. E., et al., *Virology*, 245(1):110–9 (1994). In addition, Ebola virus GP may share a common mechanism of mediating viral infection with retroviral and influenza glycoproteins. Weissenhorn, W., et al., *Mol Membr Biol*, 16(1):3–9 (1999). Because membrane-bound GPs play critical roles in initiating virus infection and are also the predominant proteins exposed on the surface of the virions, they are the primary targets for neutralizing antibodies against the virus.

One of the properties of Ebola viruses that make them lethal to the host is their ability to suppress the host immune system. Serologic analysis of patients who died of the Ebola virus infection showed no signs of humoral or cellular immune responses. Baize, S., et al., *Nat Med*, 5(4):423–6 (1999). In contrast, antibodies against viral proteins and virus-specific T-cell activities were detected in a few survivors. Baize, S., et al., *Nat Med*, 5(4):423–6 (1999). Although the immunosuppressive mechanisms are yet to be understood, it is probable that the high levels of sGP and the immunosuppressive peptide in the GP are to blame for the absence of humoral and cellular immune responses in Ebola virus-infected patients.

The proteins that are responsible for the initial inflection of Ebola virus are the viral glycoproteins. Therefore, they are the target for neutralizing antibodies. However, Ebola virus has evolved "tricks" to prevent or delay the host immune response until it is too late to recover from the infection. Conventional approaches in producing vaccines against Ebola virus are likely to be ineffective for the following reasons: (1) viral glycoproteins produced in bacteria, yeast or insect cells are not properly glycosylated and therefore do not have the true antigenicity of the viral proteins; (2) Ebola virus is too dangerous to be produced in large amounts as an inactivated-virus virus vaccine; and (3) procedures of inactivating the virus often destroy the conformation of the proteins, and therefore alter their antigenicity.

A preferred embodiment of the present invention is a recombinant viral vaccine having nucleic acids encoding one or more antigens of Ebola virus. Restriction maps and full sequence information of the Ebola virus, including the Zaire strain, is available through GenBank.

The genetic vaccine is a recombinant benign virus which is replication defective or incompetent and therefore is incapable of spreading beyond initially infected cells. For example, a recombinant adenoviral vaccine of the present invention mediates high levels of Ebola viral antigen expression for a period of two or more weeks, even though Ebola viral proteins have no functional relevance to recombinant virus function.

In another embodiment of the invention, the recombinant virus expresses one or more modified Ebola virus antigens. The modified Ebola virus antigens are preferably Ebola virus envelope glycoproteins and/or immunogically active parts thereof. Preferably the glycoproteins are modified GP and sGP glycoproteins. The Ebola virus GP and sGP glycoproteins are modified to destroy their pathogenic and immunosuppressive functions, but retain most of their natural antigenicity, since they are expressed, folded, glycosylated, and targeted to the cellular membrane inside the cells that can be productively infected by the Ebola virus. The modifications are carried out using standard molecular genetic manipulation techniques such as restriction digests and polymerase chain reaction.

A preferred modification of the Ebola virus envelope glycoprotein destroys the infective function of the Ebola virus GP. Any modification that destroys the infective function of Ebola virus can be used, but preferably the modification is a five amino acid deletion in the cleavage site of the GP. See Example 1. This cleavage site is composed of five basic amino acid residues, RRTRR, at position 501 from the start of the open reading frame. This deletion may be introduced into the Ebola virus GP cDNA using PCR amplification, which is performed by methods well known in the art.

Another preferred modification of the Ebola virus viral genome prevents synthesis of the sGP. Any modification that prevents synthesis may be employed. Preferably the modification is directed to altering the RNA editing site from UUUUUUU [SEQ ID NO: 2] to UUCUUCUU [SEQ ID NO: 3]. See example 1.

Another preferred modification to Ebola virus antigen used in the present vaccines is immunosuppressive (IS) peptide located in GP2. The IS peptide motif is located at amino acids 585–609. A ten amino acid deletion between amino acid 590–600 removes its function. Second, each half of the IS peptide motif is reversed and duplicated. See FIG. 2. This further ensures that its function has been destroyed and also increases its antigenicity.

Further it is readily apparent to those skilled in the art that variations or derivatives of the nucleotide sequences encoding Ebola virus antigen(s) of the present invention can be produced, which alter the amino acid sequence of the encoded protein. The altered expressed antigen(s) may have an altered amino acid sequence, yet still elicit immuneresponses that react with Ebola virus antigen(s), and are considered functional equivalents. In addition, fragments of the full-length genes that encode portions of the full-length protein may also be constructed. These fragments may encode a protein or peptide which elicits antibodies which react with Ebola virus antigen(s), and are considered functional equivalents.

Vaccination of an individual with the vaccines of the present invention results in entrance of adenoviral particles into cells and expression of Ebola virus antigen(s), such as the envelope glycoproteins, and the immune-stimulating cytokines. The expression of Ebola virus antigen(s) in cells induces strong and persistent immune responses as if an infection has occurred. The genetic vaccine has all of the immunogenicity of a natural infection, including expression of the natural viral proteins and long-lasting antigen stimulation, but does not have the pathogenicity of a true viral infection. In the vaccines of the present invention, the immunosuppressive mechanisms of Ebola virus are disabled, the antigens occur in their natural forms and are associated with the cell membrane, and immune stimulation lasts for weeks. The effects of this novel vaccine are long lasting and provide high rates of protection against Ebola virus infection.

The present invention is also directed to a method of immunizing a human against Ebola virus infection comprising administering the vaccines described above. The techniques for administering these vaccines to humans are known to those skilled in the health fields.

By using the genetic vaccine of the present invention, individuals may be immunized against Ebola virus. Since the genetic vaccine can express high levels of antigens and/or a variety of glycoproteins simultaneously, the vaccinated individuals should be immunized against various strains Ebola virus. Additionally, since the genetic vaccine can express high levels of cytokines to mimic the body's response to natural viral infection, the body's immune response to such a genetic vaccine against Ebola virus should be strong and long-lasting, thereby achieving a life-long immunity against the Ebola virus.

5. Formulation and Routes of Administration

The present invention also relates to a pharmaceutical composition comprising the vaccine(s) described above, and a pharmaceutically acceptable diluent, carrier, or excipient carrier. Additionally the vaccine may also contain an aqueous medium or a water containing suspension, often mixed with other constituents in order to increase the activity and/or the shelf life. These constituents may be salt, pH buffers, stabilizers (such as skimmed milk or casein hydrolysate), emulsifiers, and preservatives.

An adjuvant may be included in the pharmaceutical composition to augment the immune response to the viral antigen expressed from the recombinant virus. Examples of the adjuvant include, but are not limited to, muramyl dipeptide, aluminum hydroxide, saponin, polyanions, anamphipatic substances, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believed to reduce tumor-induced suppression when given in low doses.

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention can be administered in a conventional active immunization scheme: single or repeated administration in a manner compatible with the dosage formulation, and in such amount as will be prophylactively effective, i.e. the amount of immunizing antigen or recombinant microorganism capable of expressing the antigen that will induce immunity in humans against challenge by the pathogenic virus or bacteria, such virulent Ebola virus, HIV, hepatitis A, B, C, D, and E virus, and bacillus tuberculous. Immunity is defined as the induction of a significant level of protection after vaccination compared to an unvaccinated human.

The vaccine of the present invention, i.e. the recombinant virus, may be administered to a host, preferably a human subject, via any pharmaceutically acceptable routes of administration. The routes of administration include, but are not limited to, intramuscular, intratracheal, subcutaneous, intranasal, intradermal, rectal, oral and parental route of administration. Routes of administration may be combined, if desired, or adjusted depending upon the type of the pathogenic virus to be immunized against and the desired body site of protection.

Doses or effective amounts of the recombinant virus may depend on factors such as the condition, the selected viral or bacterial antigen, the age, weight and health of the host, and may vary among hosts. The appropriate titer of the recombinant virus of the present invention to be administered to an individual is the titer that can modulate an immune response against the viral or bacterial antigen and elicits antibodies against the pathogenic virus or bacteria from which the antigen is derived. An effective titer can be determined using an assay for determining the activity of immunoeffector cells following administration of the vaccine to the individual or by monitoring the effectiveness of the therapy using well known in vivo diagnostic assays. For example, a prophylactically effective amount or dose of a recombinant adenovirus of the present invention may be in the range of from about 100 $\mu$ to about 10 ml of saline solution containing concentrations of from about $1\times10^4$ to $1\times10^8$ plaque forming units (pfu) virus/ml.

One skilled in the art understands that the amount of virus particles to be administered depends, for example, on the number of times the vaccine is administered and the level of response desired.

6. Methods of Enhancing the Immunity of a Host to Pathogens

The present invention also provides methods for enhancing the immunity of a host host to pathogens with the recombinant viruses described above.

In one embodiment, the method is provided for enhancing the immunity of a host host to a pathogenic virus. The method comprises: administering to the host a recombinant virus in an amount effective to induce an immune response. The recombinant virus comprises: an antigen sequence heterologous to the benign virus that encodes a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the benign virus that encodes an immuno-stimulator whose expression in the host enhances the immunogenicity of the viral antigen. The recombinant virus may preferably be replication-incompetent and not cause a malignancy naturally associated with the pathogenic virus in the host.

The recombinant virus may be administered to the host via any pharmaceutically acceptable route of administration. The recombinant virus may be administered to the host via a route of intramuscular, intratracheal, subcutaneous, intranasal, intradermal, rectal, oral and parental administration.

In another embodiment, a method is provided for immunizing a host against a pathogenic virus with multiple antigens that elicit strong and long-lasting immune response to the multiple antigens. The method comprises: administering to the host a recombinant virus in an amount effective to induce an immune response. The recombinant virus comprises: a plurality of antigen sequences heterologous to the recombinant virus, each encoding a different viral antigen from one or more pathogenic viruses, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy that is naturally associated with the pathogenic virus(es) in the host.

Optionally, the recombinant virus may also comprise one or more immuno-stimulator sequences heterologous to the recombinant virus that encodes an immuno-stimulator whose expression in the host enhances the immunogenicity of the viral antigen.

In yet another embodiment, a method is provided for immunizing a host against a pathogenic virus by using multiple genetic vaccines or viruses. Multiple recombinant viruses may carry different antigens in each recombinant virus. The multiple recombinant viruses may be administered simultaneously or step-wise to the host.

The method comprises: administering to a host a first and second recombinant viruses in an amount effective to induce an immune response, wherein antibodies are produced. The first recombinant benign virus comprises: an antigen sequence heterologous to the first recombinant virus that encodes a viral antigen from a pathogenic virus, expression of the viral antigen eliciting an immune response directed against the viral antigen and cells expressing the viral antigen in the host upon infection of the host by the recombinant virus. The second recombinant virus comprises: an immuno-stimulator sequence heterologous to the second recombinant virus that encodes an immuno-stimulator whose expression in the host enhances the immunogenicity of the viral antigen. The first and second recombinant viruses may preferably be replication-incompetent and not cause malignancy naturally associated with the pathogenic virus in the host.

According to the embodiment, the first and second recombinant virus may be any of a benign virus, such as replication-incompetent adenovirus, adeno-associated virus, SV40 virus, retrovirus, herpes simplex virus and vaccinia virus. Optionally, both the first and second recombinant viruses may be replication-incompetent adenovirus. Also optionally, one of the first and second recombinant viruses may be recombinant adenovirus and the other may be recombinant vaccinia virus.

In yet another embodiment, a method is provided for enhancing the immunity of a host to a pathogen. The method comprises: administering to the host a recombinant virus and one or more immuno-stimulators. The recombinant virus may be any of the recombinant viruses described above. In particular, the recombinant virus comprises one or more antigen sequences heterologous to the recombinant virus that encode one or more antigens from the pathogen. Expression of the antigen elicits an immune response directed against the antigen and cells expressing the antigen in the host upon infection of the host by the recombinant virus. The recombinant virus is preferably replication-incompetent and does not cause a malignancy naturally associated with the pathogen in the host. The pathogen may be a pathogenic virus such as HIV, hepatitis virus and Ebola virus, a pathogenic bacteria or parasite.

According to this embodiment, the immuno-stimulator may be any molecule that enhances the immunogenicity of the antigen expressed by the cell infected by the recombinant virus. Preferably, the immuno-stimulator is a cytokine, including, but not limited to interleukin-2, interleukin-8, interleukin-12, β-interferon, λ-interferon, γ-interferon, granulocyte colony stimulating factor, granulocyte-macrophage colony stimulating factor, and combinations thereof. The cytokine may be administered into the host in a form of purified protein. Alternatively, the cytokine may be administered in a form of expression vector that expresses the coding sequence of the cytokine upon transfecting or transducing the cells of the host.

Standard procedures for endonuclease digestion, ligation and electrophoresis are carried out in accordance with the manufacturer's or supplier's instructions. Standard techniques are not described in detail and will be well understood by persons skilled in the art.

Practicing the present invention employs, unless otherwise indicated, conventional methods of virology, microbiology, molecular biology and recombinant DNA techniques within the skill of the art. Such techniques are explained fully in the literature. See e.g. Sambrook, et al. *Molecular Cloning: A laboratory Manual; DNA Cloning: A Practical Approach*, vol I & II (D. Glover ed.); *Oligonucleotide Synthesis* (N. Giat, ed.); *Nucleic Acid Hybridization* (B. Hames & S. Higgins, eds., Current Edition); *Transcription and Translation* (B. Hames & S. Higgins, eds., Current Edition); *Fundamental Virology*, 2nd Edition, vol. I & II (B. N. Fields and D. M. Knipe, eds.)

The following examples are provided to illustrate the present invention without, however limiting the same thereto.

EXAMPLES

The following procedures are described to illustrate how to make a genetic vaccine of the present invention. The genetic vaccine is based on an adenoviral vector with modified antigens derived from Ebola virus inserted into the adenoviral backbone. Additionally, the recombinant adenovirus also carries multiple genes encoding various cytokines. The recombinant adenovirus is replication-incompetent but still retains adenoviral infectivity.

It is noted that genetic vaccine against HIV, hepatitis virus, pathogenic bacteria, and other kinds of pathogenic virus may be constructed by one with ordinary skill in the art following similar procedures described in details below.

1) Genetic Modification of the Ebola Virus Membrane Glycoproteins

The modifications are carried out using standard molecular genetic manipulation techniques, such as restriction enzyme digests and polymerase chain reaction (PCR).

The glycoproteins of Ebola virus are modified to produce the optimal antigen for Ebola virus vaccine. Two modified forms of the GP proteins are constructed to have inactivated immunosuppressive and infectious mechanisms, but retain full natural antigenicity of the wild-type glycoproteins. The mRNA editing signal is deleted to prevent the production of the secreted glycoprotein (sGP), which is immunosuppressive; and (2) the proteolytic cleavage site of the glycoprotein precursor is deleted to prevent the formation of the functional glycoproteins (GP1 and GP2). Sanchez, A., et al., *Proc Natl Acad Sci U.S.A.* 93(8):3602–7 (1996). In one form the immunosuppressive peptide region is deleted to prevent its function, and in the other form, the immunosuppressive peptide motif is split in order to destroy its function, but retain its immunogenicity. These steps produce effective and safe antigens for the vaccine.

The envelope glycoproteins (GP) of the Ebola virus are synthesized as a single precursor protein and cleaved into the two subunits (GP1 and GP2) by a cellular enzyme (furin) during transport. Volchkov, V. E., et al., *Proc Natl Acad Sci U.S.A.*, 95(10):5762–7 (1998). This proteolytic cleavage is essential for the formation of the mature glycoproteins and the release of the fusion peptide located at the C-Terminus of the cleavage site. The mature glycoproteins are incorporated into virions as trimers (each monomer is a heterodimer of GP1 and GP2 linked by a disulfide bond). Sanchez, A., et al., *J. Virol* 72(8):6442–7 (1998). The glycoproteins of Ebola virus are the major proteins exposed on the viral membrane surface, and are responsible for initiating virus entry into host cells. Therefore, they are a primary target for neutralizing antibodies.

The glycoprotein cleavage site is composed of five basic amino acid residues (RRTRR) at position 501 from the start site of the open reading frame. The Ebola virus glycoprotein cleavage site is similar to the conserved sequences found in glycoproteins of other viruses, such as in the envelope protein of RSV or MuLV. We have previously shown that deletions or point mutations at these basic amino acid residues can block cleavage and render the glycoproteins non-functional in RSV. Dong, J. Y, et al., *J. Virol* 66(2):865–74 (1992).

To destroy the infective functions of the Ebola virus glycoprotein, the five basic amino acid residues in the cleavage site are deleted. This deletion is introduced into the Ebola virus GP cDNA using PCR amplification. Alternatively, the cleavage site can be altered, such as by site specific mutation resulting in elimination of cleavage.

Another important feature of the Ebola virus is that two forms of glycoproteins are synthesized from a single gene, a secreted from (sGP) and a membrane-bound form (GP). The two forms are generated as a result of an alternative RNA editing event at a sequence of seven uridines (at location 1020–1028 from the start site), which is highly conserved among all four Ebola virus subtypes. Sanchez, A., et al., *Proc Natl Acad Sci U.S.A.* 93(8):3602–7 (1996). The sGP is synthesized from un-edited mRNA and likely has immunosuppressive functions. The GP is synthesized from an edited mRNA and likely has immunosuppressive functions. The GP is synthesized from an edited mRNA with insertion in one of the seven uridines. This RNA editing causes a frame-shift and results in a translation of the second reading frame that encodes the complete transmembrane glycoprotein (GP2).

To prevent the synthesis of sGP, the RNA editing site is modified from UUUUUUU [SEQ ID NO: 2] to UUCUUCUU [SEQ ID NO: 3]. In the cDNA, the equivalent sequence is AAAAAAA [SEQ ID NO: 4] and AAGAAGAA [SEQ ID NO: 5], respectively. This modification accomplishes two things: (1) all mRNAs encode only the GP (equivalent to the edited form with –1 frame shift); and (2) UUUUUU [SEQ ID NO: 6] encodes the same animo acid residues as UUCUUC [SEQ ID NO: 7], but prevents the possibility of further polymerase slipping at the stretch of the six uridines. The additional editing would cause deletion of one more uridine and further (–2) frame shifting. The mechanism of this modification is diagramed in FIG. 2.

A third modification may be introduced into the Ebola virus glycoprotein relating to a deletion of the immunosuppressive (IS) peptide located in GP2. The IS peptide motif (amino acid 585–609, form the start site) is highly conserved in filoviruses and has a high degree of homologywith a motif in the glycoproteins of oncogenic retroviruses that has been shown to be immunosuppressive. Volchkov, V. E., et al., *FEBS Lett* 305(3):181–4 (1992); Will, C., et al., *J. Virol* 67(3):1203–10 (1993); Mitani, M., et al., *Proc Natl Acad Sci U.S.A.* 84(1):237–40 (1987); Gatot, J. S., et al., *J. Biol Chem* 273(21):12870–80 (1998); Denner, J., et al., *J Acquir Immune Defic Syndr Hum Retrovirol* 12(5):442–50 (1996). First, a ten amino acid deletion is introduced in the core region of the motif (between amino acid 590–600) to remove its function. Second, each half of the motif is reversed and duplicated to destroy function and increase antigenicity. It is believed that antibodies against the IS peptide may inhibit the immunosuppressive function of the Ebola viruses during an infection. The basic strategy of this modification is diagrammed in FIGS. 3A–3C.

Figures 3A, 3B, 3C:
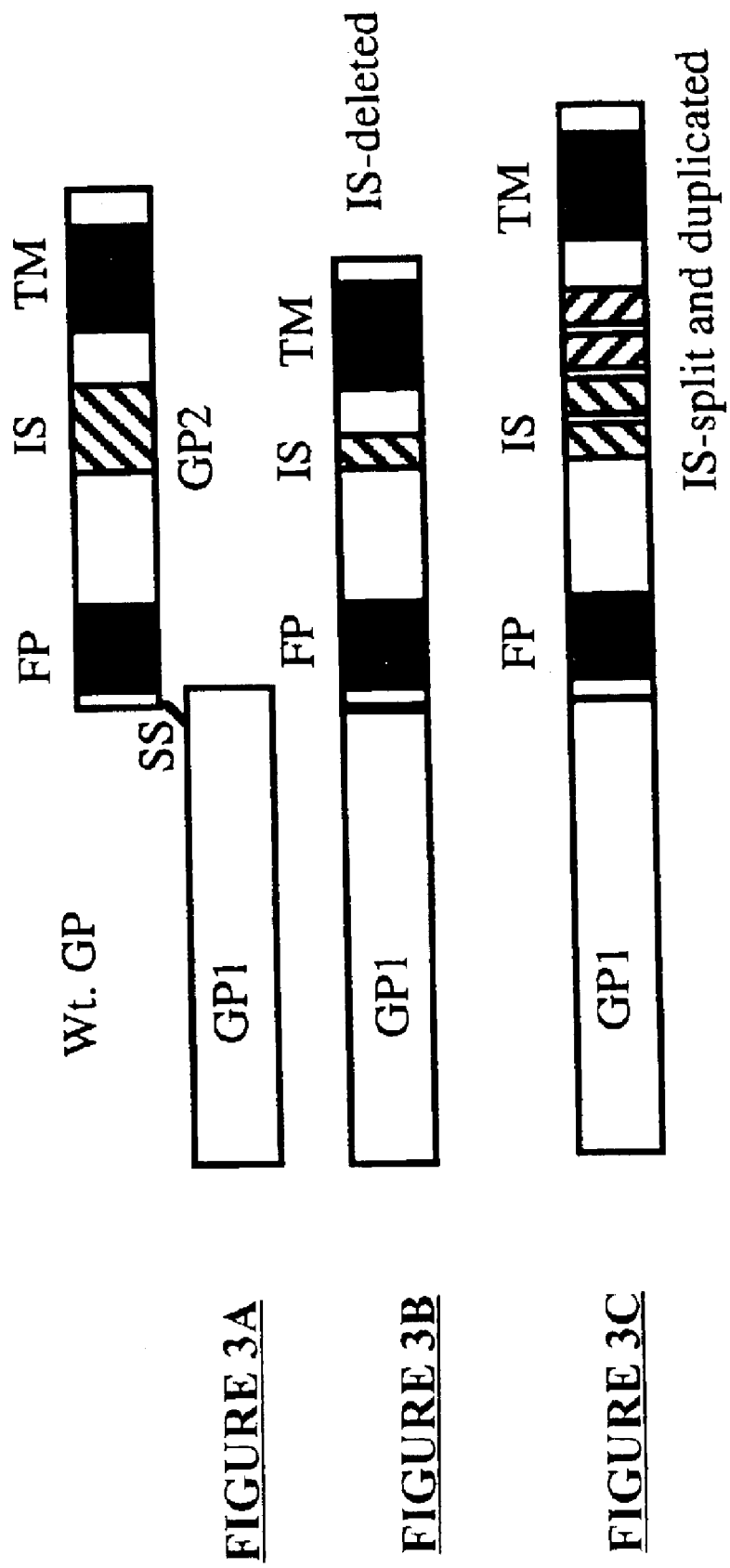
FIG. 3A shows the wild type GP.
FIG. 3B shows GP with the 10 amino acid deletion of the IS peptide.
FIG. 3C shows the IS peptide, which is split, reversed and duplicated. Abbreviations: FP, Fusion peptide; IS, Immunosuppressive peptide; TM, Transmembrane domain.

As illustrated in FIGS. 3A–3C, modification of the immunosuppressive peptide (IS) is made on the GP2 gene. FIG. 3A illustrates the wild type GP. FIG. 3B illustrates GP with the 10 amino acid deletion of the IS peptide. FIG. 3C illustrates the IS peptide, which is split, reversed and duplicated.

With these modifications, Ebola virus glycoproteins are generated that are non-functional, not immunosuppressive, yet they retain the natural antigenicity of GP. These modified GP sequences are used to generate antigens in the vaccines of the present invention against Ebola virus.

DNA sequences of the resulting altered GP genes are confirmed by sequence analysis. The modified GP sequences are then cloned intoplasmid vectors containing DNA elements necessary for efficient expression of these GPs in hostian cells. Expression and correct localization to the cellular membrane is determined by transient transfections of HeLa or 293 cells and analyzed by Western blot and FACS, using polyclonal antibodies from hyperimmunized equine serum and antihorse secondary antibodies labeled with horse radish peroxidase (HRP) or fluorescent tags, respectively.

2) Construction of a Series of Replication-defective Adenoviral Vaccines that Mediate High Levels of Expression of the Modified Ebola Virus GPs The vaccines of the present invention utilize a recombinant benign virus to carry modified antigens of Ebola virus to trick the host into mounting a robust immune defense against the Ebola virus. The preferred benign virus is a replication-defective adenovirus. These vectors are an excellent choice for vaccine expression, for several reasons. First, adenoviral vectors direct high levels of antigen expression that provide strong stimulation of the immune system. Second, the antigen that they express is processed and displayed in the transduced cells in a way that mimics pathogen-infected cells. This phase is believed to be very important in inducing cellular immunity against infected cells, and is completely lacking when conventional vaccination approaches are used. Third, adenoviral vectors infect dendritic cells which are very potent antigen-presenting cells. Diao, J. et al., *Gene Ther* 6(5):845–53 (1999); Zhong, L., et al., *Eur J Immunol* 29(3):964–72 (1999); Wan, Y., et al., *Int J Oncol* 14(4):771–6 (1999); Wan, Y., et al., *Hum Gene Ther* 8(11):1355–63 (1997). Fourth, these vectors can be engineered to carry immunoenhancing cytokine genes to further boost immunity. Fifth, adenoviruses naturally infect airway and gut epithelial cells in humans, and therefore the vaccine may be delivered through nasal spray or oral ingestion. And finally, the adenoviral vectors of this invention are safe because they are replication-defective and have been used in high doses ($10^9$ to $10^{12}$ i.p./dose) in clinical trials for gene therapy studies. Gahery-Segard, H., et al.,*J. Clin Invest* 100(9):2218–26 (1997); Bellon, G.,et al., *Hum Gene Ther* 8(1):15–25 (1997); Boucher, R. C., et al., *Hum Gene Ther* 5(5):615–39 (1994). Indeed, even live viruses have been safely used in military recruits to prevent common colds.

This vector-construction system is also used to establish complex vectors that express multiple genes or regulatory mechanisms. For example, the vector construct is used to express multiple cytokines along with Ebola GP antigens in a single complex vector to further enhance the immune induction. Alternatively, antigens and cytokines are placed in separate vectors. This enables the manipulation of different combinations of cytokines and antigens by co-transduction (infection) with two or three vectors.

Figure 4A:
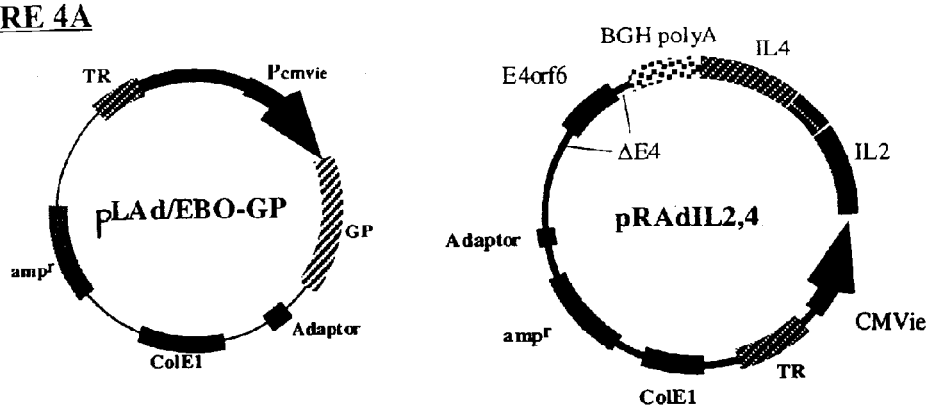
FIGS. 4A and 4B illustrate a procedure used to create a recombinant adenoviral vector as a genetic vaccine against Ebola virus.

Construction of the adenoviral vectors is diagramed in FIG. 4. The cDNA encoding a modified GP(s) is cloned into the left-end (E1 region) of the adenovirus genome using a shuttle vector pLAd (FIG. 4A left side), resulting in a shuttle vector pLAd/EBO-GP. The pLAd/EBO-GP vector contains the left end of the adenoviral genome including the left long terminal repeats L-TR and the adenoviral packaging signal ψ. Genes encoding cytokines such as IL-2 and IL-4 are inserted into E4 region of the adenovirus vector using the shuttle vector pRAd (FIG. 3A right hand), resulting in a shuttle vector pRAdIL2,4. The pRAdIL2,4 contains the right end of the adenoviral genome including the right long terminal repeats RTR.

To construct an adenoviral vector carrying the GP gene only, the shuttle vector pLAd/EBO-GP is digested with appropriate restriction enzymes such as Xba I. The fragment containing the GP gene is ligated to an adenoviral backbone and pRAd vector.

Figure 4B:
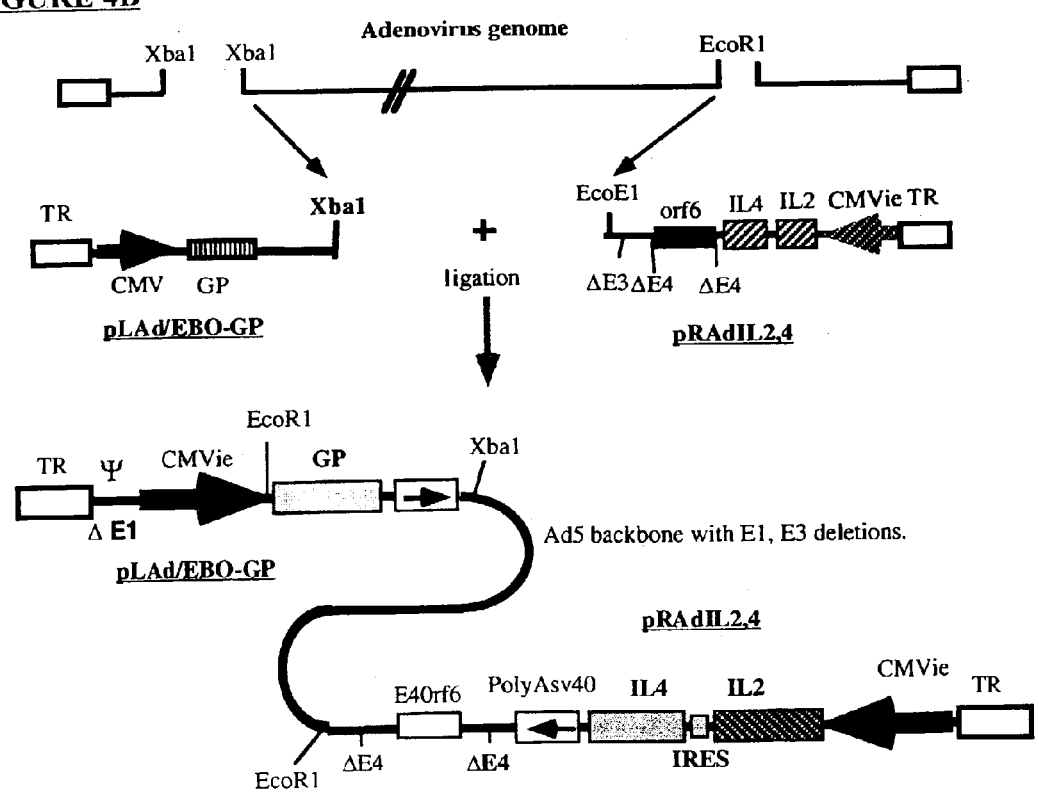

To construct an adenoviral vector carrying both the GP gene in the E1 region and cytokine genes in the E4 region, both pLAd/EBO-GP and pRAdIL2, 4 are linearized and ligated to the backbone of the adenovirus (FIG. 4B).

To generate recombinant adenoviral vectors, the ligated vector genome is transfected into 293 cells, in which only the correctly ligated genome with the two adenovirus terminal repeats can replicate and generate infectious viral particles. Human 293 cells (Graham et al., *J. Gen. Virol.*, 36: 59–72 (1977)), available from the ATCC under Accession No.: CRL1573), has adenovirus E1a and E1b genes stably integrated in its genome. The 293 cells supplement the essential E1 gene of adenovirus that has been deleted from the vector backbone. The final vector has E1, E3 and partial E4 deleted and can only replicate in 293 cells, but not in target cells. The adenoviral vectors are amplified in 293 cells and purified by ultracentrifugation in cesium chloride gradients. Titers of vectors are determined by serial dilutions and counting of the infectious particle (ip) after infection of 293 cells.

3) Determination of Immune Respones to the Genetic Vaccine

An in vitro assay is used to quantitate the amount of neutralizing antibodies developed in response to the vaccine. The assay is based on a retroviral vector system which is based on a Moloney Murine Leukemia virus system. Vectors and packaging cells expressing GAG and POL proteins have been extensively characterized and are commercially available. A packaging vector construct that carries a β-galactosidase gene as a reporter is used. A novel vector construct expressing the membrane form of the Ebola virus GP is co-transfected with the β-gal reporter vector resulting in a GAG-POL packaging cell line, which generates retroviral vector particles with the Ebola virus GP instead of its original envelope protein.

4) Determination of which Modified GP Antigen Provides Better Production of Neutralizing Antibodies in Animal Models The adenoviral vaccine vectors carrying the two GP variants are tested for their ability to induce an immune response to the Ebola virus GP in CD-1 mice (Charles River Laboratories; outbred stock of Swiss mice from Rockefeller Institute). Specifically, the neutralizing antibody titers and cytolytic T-lymphocyte (CTL) activities to the Ebola virus GP antigens induced by the GP variants with and without the IS motif are compared. Three groups of 30 8-week old mice are injected subcutaneously with $10^5$ ip of adenoviral vectors expressing GP variant 1 (with IS peptide deleted), GP variant 2 (with IS peptide split and inverted) and β-Galactosidase (control vector), respectively. Six mice from each group are sacrificed (by $CO_2$ asphyxiation and cervical dislocation) at 1, 2, 4, 8 and 16 weeks post-vaccination, and their blood and spleens are harvested. In addition, 6 mice are mock-vaccinated with saline and sacrificed 2 days later to provide preimmunization controls.

From mice injected with the control β-Gal vector, tissue sections from the sites of the vector injection are taken, fixed, and stained with the X-gal solution to determine the number and type of vector-transduced cells at various timepoints post-infection. In addition, hemolysin staining isperformed to determine the degree of infiltration of various immune cells (neutrophils, macrophages, monocytes, etc.) at the site of the vector delivery.

Sera from vaccinated animals is assayed for total GP-binding antibodies using a standard 96-well plate ELISA protocol, as has been described. Van Ginkel, F. W., et al., *Hum Gene Ther* 6(7):895–903 (1995); Van Ginkel, F. W., et al., *J Immunol* 159(2):685–93 (1997). Neutralizing activity of the sera is analyzed by monitoring the infectious activity of the Ebola virus GP-pseudotyped retroviral vector (Wool-Lewis, et al., *J. Virol*, 72(4):3155–60 (1998)) on HeLa cells after the vector has been incubated with various serum concentrations. Expression of β-galactosidase in infected cell lysates serves as an indicator of the neutralizing activity of the serum (the lower the β-gal activity, the more EBO-β-Gal vectors have been neutralized) and is measured using a very sensitive fluorogenic substrate (Galacto-Light kit J) and a fluorescence plate reader. Anti-GP serum-neutralized infection rates are compared to infection rates in the absence of serum and in the presence of non-GP activated serum.

Cytotoxic lymphocytes (CTLs) are extracted from mouse spleens as has been previously described. Van Ginkel, F. W., et al., *Hum Gene Ther* 1995;6(7):895–903; Dong, J. Y., et al., *Hum Gene Ther* 1996;7(3):319–31. They are mixed with a constant number of detached LnCaP cells (prostate carcinoma cells of epithelial origin) transduced with an adenoviral vector carrying an unmodified Ebola virus GP protein. Ratios of effector: target cells of 10:1, 3:1, and 1:1 are used. The cells are seeded into 96-well plates, and 24 hour later all unattached cells (which include all of the effector CTLs and dead or dying LnCaP cells) are removed, and the remaining viable (adherent) cells are quantitated by the MTT (3-(4,5-dimethylthiazol-20-yl) 2,5-diphenyl tetrazolium bromide) cleavage assay. This assay has been employed in detecting the lymphocyte cytotoxic activity (Ni, J., et al., *J Clin Lab Anal* 1996;10(1):42–52) and compares favorably with the radioactive assays in terms of sensitivity, reliability and speed.

5) Immunoenhancing Functions of Multiple Cytokines and Their Effect on the Efficacy of the Bioengineered Vaccines To augment the effects of the vaccine, a vector-mediated gene transfer to express the immunoenhancing cytokines, such as IL2, IL4, IL12, INF-γ, and GM-CSF is used. Initially, each cytokine is separately cloned or the cytokines are cloned in various combinations into adenoviral vectors separate from the vectors encoding viral antigens. The immunoenhancing effects of individual cytokines or their combinations are studied by co-infecting with a vector encoding the cytokine and the vector carrying the antigens. The titers of serum antibodies are compared, as well as the time it takes to reach effective titers in animals inoculated with vaccines in combination with different cytokine-expressing vectors. These experiments allow the determination of whether immunoenhancing cytokines induce higher levels of antibodies, shorten the induction time, and prolong the immunity against the Ebola virus.

After determining the best-performing modified GP variant, the extent that the immune response elicited by it is enhanced by co-delivery to the immunization site of vectors carrying various cytokines is analyzed. Interleukin-2, either by itself or in combination with IL-4 or IL-12, has been demonstrated to strongly enhance the activation and proliferation of cytotoxic T-cells, natural killer (NK) cells and B-cells. Michael, B. N., et al., *Cell Immunol* 1994;158(1);105–15; Bruserud, O., et al., *Eur J. Haematol* 1992;48(4);221–7; Jacobsen, S. E., et al., *Res Immunol* 1995;146(7–8):506–14; Wolf, S. F., et al., *Res Immunol* 1995;146(7–8);486–9; Tepper, R. I., *Res Immunol* 1993;144 (8):633–7; O'Garra A., et al., *Res Immunol* 1993;144(8):620–5; Ohe, Y., et al., *Int J Cancer* 1993;53(3):432–7; Delespesse, G., et al., *Res Immunol* 1995;146(7–8):461–6. [36–43]. INF-γ stimulates the humoral immune response and increases the permeability of the blood vessel walls at the site of its secretion (Chensue, S. W., et al., *J Immunol* 154(11):5969–76 (1995); Szente, B. E., et al., *Biochem Biophys Res Commun* 203(3):1645–54 (1994); Adams, R. B., et al., *J. Immunol* 150(6):2356–63 (1993)), while Gm-CSF activates and attracts macrophages and other professional APCs to the site of the infection. Bober, L. A., et al., *Immunopharmacology* 29(2):111–9 (1995); Dale, D. C., et al., *Am J. Hematol* 57(1):7–15 (1998); Zhao, Y., et al., *Chung Hua I Hsueh Tsa Chih* 77(10): 32–6 (1997).

Six groups of 30 8-week old mice are injected subcutaneously with a mixture of $5\times10^4$ ip of the selected GP variant vector and $5\times10^4$ ip of one of the following vectors: Ad-β-Gal, Ad-IL2, Ad-IL2/IL4, Ad-IL2/IL12, Ad-IFN-γ and Ad-GM-CSF.

Six mice from each group are sacrificed and analyzed at 1, 2, 4, 8 and 16 weeks as described in Example 4. Analysis of total IgG is peformed using ELISA, neutralizing activity is assayed as interference with the ability of EBO-GP pseudotyped retroviral vector to infect HeLa cells, and anti-GP CTL activity is performed by mixing spleen-extracted CTLs with target LnCaP cells transduced with Ad-EBO-GP construct as described in Example 4. Levels of various cytokines in the serum are also quantitated by ELISA using available commercial assays. In some cases, these assays can distinguish between human and murine versions of the same cytokine, providing direct information on the expression levels of cytokines delivered using Adenovirus vectors and how they correlate with the development of the immune response.

After the individual cytokines are analyzed, those that performed best are tested in combinations. Four groups of 30 8-week old mice are injected subcutaneously with a mixture of $5\times10^4$ i.p. of the selected GP variant vector and $5\times10^4$ i.p. of up to 3 selected cytokine-expressing vectors (if fewer than 3 cytokine vectors are used, i.p. counts are made up with Ad-β-Gal vector). Six mice from each group are sacrificed at weeks 1, 2, 4, 8 and 16, and analyzed as described above.

To verify the robust and reproducible nature of the immune response to the GP vector and multiple cytokines in different species, the experiment as described above is reproduced in rabbits. Five groups of six white New Zealand rabbits are injected into the thigh muscle with one of the following vector combinations: the Ad-β-Gal vector ($10^6$ ip), the selected GP vector ($2.5\times10^5$ ip plus $7.5\times10^5$ ip of Ad-β-Gal), and three cytokine vector combinations ($2.5\times10^5$ of each cytokine vector) plus the GP vector ($2.5\times10^5$ ip), as described above. The animals are bled 2 days prior to vaccination (pre-immune bleed) and then according to the schedule described above. 5 to 10 ml of blood will be extracted per session. Analysis is performed in a similar fashion to that of mice (see above).

Because genes coding for human cytokines are used in mouse and rabbit models, it is possible that their immune systems will have a non-identical (to human) response to those proteins. However, a high degree of homology exists between human and mouse cytokines and their receptors, and published reports on experiments using human or other hostian cytokines in mice indicate a high level of equivalency. If necessary, species-specific versions of these cytokines can be obtained and cloned into the adenoviral vectors of the present invention for species-targeted cytokine activity studies.

6) Optimizing the Efficiency and Rates of Administration of the Vaccine and Conducting Safety and Pathogen Challenge Studies in Non-Primate and Primate Animal Models After determining the best combinations of the cytokines and antigens, the final version of the vaccine vectors are constructed. These complex recombinant adenoviral vectors deliver combinations of cytokines and antigens into target cells using a single vector. Dose-titer analysis in mice and rabbits are conducted to identify the lowest dose required to generate maximallevels of immune responses. Different routes of vaccine administration, such as intramuscular and intravenous injection, oral ingestion and nasal sprays are compared. For safety studies, dose escalation experiments in mice and rabbits are conducted until toxicity is observed or until levels ten times the effective dose have been reached. Finally, additional safety and pathogen challenge experiments are conducted in primates.

What is claimed is:

1. A method of producing an immune response in a host to a pathogen, comprising the step of:
administering to the host a recombinant adenovirus comprising (a) an antigen sequence that is heterologous to a native progenitor of the recombinant adenovirus and encodes a first viral antigen from a first pathogenic virus and a second viral antigen from a second pathogenic virus, said first and second viral antigens being expressed bicistronically under the transcriptional control of a first promoter located in the same region as the antigen sequence; and (b) an immuno-stimulator sequence that is heterologous to the native progenitor of the recombinant adenovirus and encodes a first immuno-stimulator expressed under the transcriptional control of a second promoter located in the same region as the immuno-stimulator sequence, wherein the antigens and immuno-stimulatory sequences are inserted into separate regions of said adenovirus, wherein said regions are selected from group consisting of E1, E3 and E4 that are partially or entirely deleted to render the recombinant adenovirus replication-incompetent, and expression of the antigen and immuno-stimulator sequences elicits an immune response directed against the first or second viral antigen upon infection of the host by the recombinant virus.

2. The method of claim 1, wherein the antigen sequence and the immuno-stimulator sequence are positioned in the E1 and E3 regions of the native progenitor of the recombinant adenovirus, respectively.

3. The method of claim 1, wherein the antigen sequence and the immuno-stimulator sequence are positioned in the E1 and E4 regions of the native progenitor of the recombinant adenovirus, respectively.

4. The method of claim 1, wherein the antigen sequence and the immuno-stimulator sequence are positioned in the E3 and E4 regions of the native progenitor of the recombinant adenovirus, respectively.

5. The method of claim 1, wherein the first promoter is a promoter homologous to the native progenitor of the recombinant adenovirus.

6. The method of claim 1, wherein the first or second promoter is a promoter heterologous to the native progenitor of the recombinant adenovirus.

7. The method of claim 1, wherein the first or second promoter is heterologous to the native progenitor of the recombinant adenovirus and is a promoter selected from the group consisting of CMV promoter, SV40 promoter, retrovirus LTR promoter, and chicken cytoplasmic b-actin promoter.

8. The method of claim 1, wherein the first and second antigen sequences are expressed bicistronically via an internal ribosomal entry site or via a splicing donor-acceptor mechanism.

9. The method of claim 1, wherein the first or second pathogenic virus is a human immunodeficiency virus.

10. The method of claim 9, wherein the first or second viral antigen is an HIV surface, core/capsid, regulatory, enzyme or accessory protein.

11. The method of claim 9, wherein the first or second viral antigen is selected from the group consisting of HIV gp120, gp41, Gag, p17, p24, p2, p7, p1, p6, Tat, Rev, PR, RT, IN, Vif, Vpr, Vpx, Vpu and Nef.

12. The method of claim 1, wherein the first or second viral antigen is a full-length antigenic viral protein or a portion of the antigenic viral protein that contains the predominant antigen, neutralizing antigen, or epitope of the pathogenic virus.

13. The method of claim 1, wherein the first or second viral antigen is a modified antigen that is mutated from a glycoprotein of the pathogenic virus such that the viral antigen is rendered non-functional as a viral component but retains its antigenicity.

14. The method of claim 13, wherein the modification of the first or second viral antigen includes deletions in the proteolytic cleavage site of the glycoprotein, and duplication and rearrangement of immunosuppressive peptide regions of the glycoprotein.

15. The method of claim 1, wherein the native E4 region of the recombinant adenovirus except ORF6 is deleted.

16. The method of claim 1, wherein the native E1 region of the recombinant adenovirus is completely deleted, the native E3 of the recombinant adenovirus is functionally deleted, and the native E4 region of the recombinant adenovirus except ORF6 is deleted.

17. The method of claim 1, wherein the immuno-stimulator is a cytokine.

18. The method of claim 17, wherein the cytokine is selected from the group consisting of interleukin-2, interleukin-4, interleukin-12, b-interferon, 1-interferon, g-interferon, granulocyte colony stimulating factor, and granulocyte-macrophage colony stimulating factor.

19. The method of claim 1, wherein the immuno-stimulator sequence further encodes a second immuno-stimulator that is expressed bicistronicaily by the second promoter.

20. The method of claim 19, wherein the second immuno-stimulator is expressed by the second promoter bicistronically via an internal ribosomal entry site or via a splicing donor-acceptor mechanism.

* * * * *